US008232359B2

(12) United States Patent
Ok et al.

(10) Patent No.: US 8,232,359 B2
(45) Date of Patent: *Jul. 31, 2012

(54) PROCESS FOR PREPARING ETHYLENE HOMOPOLYMERS OR COPOLYMERS OF ETHYLENE WITH α-OLEFIN BY USING THE TRANSITION METAL COMPOUND

(75) Inventors: Myungahn Ok, Daejeon (KR); Dongcheol Shin, Daejeon (KR); Jisu Jeong, Daejeon (KR); Hoseong Lee, Daejeon (KR); Jongsok Hahn, Daejeon (KR); Choonsik Shim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/223,636

(22) Filed: Sep. 1, 2011

(65) Prior Publication Data

US 2011/0319576 A1    Dec. 29, 2011

Related U.S. Application Data

(60) Continuation of application No. 12/981,647, filed on Dec. 30, 2010, which is a division of application No. 12/565,220, filed on Sep. 23, 2009, now Pat. No. 7,928,173.

(30) Foreign Application Priority Data

Sep. 25, 2008  (KR) .................. 10-2008-0094010
Sep. 1, 2009   (KR) .................. 10-2009-0081840

(51) Int. Cl.
*C08F 4/6592* (2006.01)
*C08F 4/642* (2006.01)
*B01J 31/22* (2006.01)

(52) U.S. Cl. ........ 526/160; 526/165; 526/172; 526/348; 526/352; 526/943

(58) Field of Classification Search .................. 526/160, 526/165, 172, 348, 943
See application file for complete search history.

(56) References Cited

U.S. PATENT DOCUMENTS

| 4,752,597 | A  | 6/1988  | Turner         |
|-----------|----|---------|----------------|
| 5,043,408 | A  | 8/1991  | Kakugo et al.  |
| 5,079,205 | A  | 1/1992  | Canich         |
| 5,198,401 | A  | 3/1993  | Turner         |
| 6,329,478 | B1 | 12/2001 | Katayama et al.|

FOREIGN PATENT DOCUMENTS

| EP | 0 372 632      | 1/1996  |
| EP | 0 320 762      | 3/1996  |
| EP | 0 416 815      | 8/1997  |
| EP | 0 420 436      | 7/2000  |
| EP | 0 842 939      | 10/2004 |
| JP | 63-092621      | 4/1988  |
| JP | 2-84405        | 3/1990  |
| JP | 3-2347         | 1/1991  |
| KR | 10-2001-0074722| 9/2001  |

OTHER PUBLICATIONS

J. Randall, "A Review of High Resolution Liquid $^{13}$Carbon Nuclear Magnetic Resonance Characterizations of Ehtylene-Based Polymers", JMS—Rev. Macromol. Chem. Phys. C29(2 & 3), 201-317 (1989).

*Primary Examiner* — Caixia Lu
(74) *Attorney, Agent, or Firm* — Clark & Brody

(57) ABSTRACT

Provided are transition metal catalytic systems for preparing ethylene homopolymers or copolymers of ethylene with α-olefins. More specifically, provided are Group 4 transition metal catalysts, which is characterized in that the catalyst comprises around the Group 4 transition metal a cyclopentadiene derivative, and at least one aryloxide ligand(s) having a fluorenyl group or a derivative thereof (which is ready to be substituted at 9-position) that functions as an electron donor and serves to stabilize the catalytic system by surrounding an oxygen atom that links the ligand to the transition metal at ortho-position, and there is no cross-linkage between the ligands; catalytic systems comprising such transition metal catalyst and aluminoxane cocatalyst or boron compound cocatalyst; and processes for preparing ethylene homopolymers or copolymers of ethylene with α-olefins by using the same.

5 Claims, No Drawings

PROCESS FOR PREPARING ETHYLENE HOMOPOLYMERS OR COPOLYMERS OF ETHYLENE WITH α-OLEFIN BY USING THE TRANSITION METAL COMPOUND

TECHNICAL FIELD

The present invention relates to transition metal catalytic systems for preparing ethylene homopolymers or copolymers of ethylene with α-olefins. More specifically, it relates to Group 4 transition metal catalyst, which is characterized in that the catalyst comprises around the Group 4 transition metal a cyclopentadiene derivative, and at least one aryloxide ligand(s) having a fluorenyl group or a derivative thereof that functions as an electron donor and serves to stabilize the catalytic system by surrounding an oxygen atom that links the ligand to the transition metal at ortho-position and has a chemical structure to be easily substituted at 9-position, and there is no cross-linkage between the ligands; catalytic systems comprising the above transition metal catalyst and aluminoxane cocatalyst or boron compound cocatalyst; and processes for preparing ethylene homopolymers or copolymers of ethylene with α-olefins by using the same.

BACKGROUND ART

Conventionally, so-called Ziegler-Natta catalysts which consist of a titanium or vanadium compound as primary catalyst component and an alkylaluminium compound as cocatalyst component have been usually employed for preparing ethylene homopolymers or copolymers of ethylene with α-olefins. Though a Ziegler-Natta catalytic system exhibits high activity on ethylene polymerization, the catalytic system is disadvantageous in that the molecular weight distribution of the produced polymer is broad owing to irregular catalyst activation point, and it may result in irregular distribution of composition, particularly in copolymers of ethylene with α-olefin.

Recently, metallocene catalytic systems consisting of a metallocene compound of Group 4 transition metal in the Periodic Table of Elements, such as titanium, zirconium and hafnium, and methyl aluminoxane as a cocatalyst have been developed. Since the metallocene catalytic system is a homogeneous catalyst having a mono-modal catalyst activation point, it can provide polyethylene having narrow molecular weight distribution and homogenous composition distribution as compared to conventional Ziegler-Natta catalyst. For example, European Patent Publication Nos. 320,762 and 3,726,325; Japanese Patent Laid-Open Nos. Sho 63-092621, Hei 02-84405 and Hei 03-2347 reported that ethylene can be polymerized with high activity by activating the metallocene compounds such as $Cp_2TiCl_2$, $Cp_2ZrCl_2$, $Cp_2ZrMeCl$, $Cp_2ZrMe_2$, ethylene$(IndH_4)_2ZrCl_2$ by using methyl aluminoxane as cocatalyst, to provide polyethylene having the molecular weight distribution (Mw/Mn) in the range from 1.5 to 2.0. However, it is difficult to obtain polymers of high molecular weight by using such a catalytic system. Particularly, when the catalytic system is applied to solution polymerization carried out at a high temperature of 140° C. or higher, the polymerizing activity abruptly decreases but β-dehydrogenation predominates, so that the system is known to be not suitable for preparing polymers having high molecular weight (weight average molecular weight, Mw) of 100,000 or more.

In the meanwhile, disclosed were so-called geo-restrictive non-metallocene type catalysts (also referred to as single activation point catalysts), wherein the transition metals are linked in the form of a ring, as catalysts for preparing high molecular weight polymers with high catalytic activity in polymerization of ethylene homopolymers or copolymerization of ethylene with β-olefin. European Patent Nos. 0416815 and 0420436 suggested the examples wherein amide group is linked in the form of a ring to one cyclopentadiene ligand, while European Patent No. 0842939 showed exemplary catalysts wherein phenolic ligand (as electron donors) is linked to cyclopentadiene ligand in the form of a ring. However, there are many difficulties to commercially utilize such catalysts since the yield of the procedure of ring formation between the ligand and the transition metal compound is very low during the synthesis of the geo-restrictive catalyst as described above.

On the other hand, examples of non-metallocene catalysts that are not geo-restrictive can be found in U.S. Pat. No. 6,329,478 and Korean Patent Laid-Open No. 2001-0074722. It is found that the catalyst of single activation point, which employs a phosphinimine compound as a ligand, showed high ethylene conversion in the copolymerization of ethylene with α-olefin under the condition of solution polymerization at a high temperature of 140° C. or more. U.S. Pat. No. 5,079,205 discloses the examples of catalysts containing bisphenoxide ligand, and U.S. Pat. No. 5,043,408 those containing bisphenoxide ligand of chelate type. However those catalysts have so little activity that can be hardly employed for industrial preparation of ethylene homopolymers or ethylene copolymers with α-olefin, which is carried out at a high temperature.

DISCLOSURE

[Technical Problem]

In order to overcome the problems of conventional techniques, the present inventors carried out extensive studies, and found that non-crosslinked type catalyst, which comprises a cyclopentadiene derivative, and at least one aryloxide ligand(s) having a fluorenyl group or a derivative thereof that functions as an electron donor and serves to stabilize the catalytic system by surrounding an oxygen atom that links the ligand to the transition metal at ortho-position and has a chemical structure to be easily substituted at 9-position, exhibits excellent catalytic activity in polymerization of ethylene with olefins. Based on the discovery, the inventors developed catalysts for preparing high molecular weight ethylene homopolymers or copolymers of ethylene with α-olefin with high activity during the process of polymerization at a temperature of 60° C. or more, and completed the present invention.

Thus, an object of the invention is to provide transition metal compounds which are useful as catalysts for preparing ethylene homopolymers or copolymers of ethylene with α-olefin, catalyst compositions comprising the same, and ethylene homopolymers or copolymers of ethylene with α-olefin which were prepared by using the compound or the catalyst composition.

Another object of the invention is to provide a process for polymerization wherein a catalyst of single activation point with high activity is employed in α-olefin polymerization, which allows economic preparation of ethylene homopolymers or copolymers of ethylene with α-olefin, having various physical properties, from the aspect of commercialization.

[Technical Solution]

To achieve the objects of the present invention, one aspect of the present invention relates to Group 4 transition metal catalysts (as represented by Chemical Formula (1)), which is characterized in that the catalyst comprises around the Group 4 transition metal a cyclopentadiene derivative, and at least one aryloxide ligand(s) having a fluorenyl group or a derivative thereof (which is ready to be substituted at 9-position) that functions as an electron donor and serves to stabilize the catalytic system by surrounding an oxygen atom that links the ligand to the transition metal at ortho-position, and there is no cross-linkage between the ligands; catalytic systems comprising such transition metal catalyst and aluminoxane cocatalyst or boron compound cocatalyst; and processes for preparing ethylene homopolymers or copolymers, of ethylene with α-olefins by using the same.

[Chemical Formula 1]

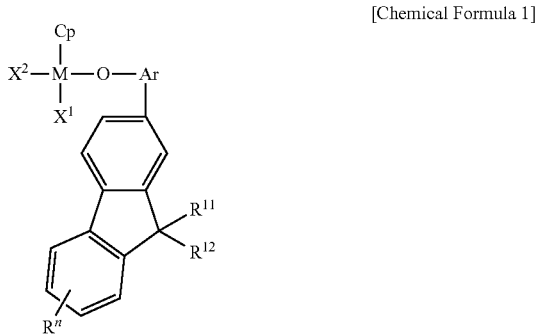

In the formula, M represents transition metal from Group 4 in the Periodic Table of Elements;

Cp represents cyclopentadienyl ring which is $\eta^5$-linkable to M, or a fused ring containing a cyclopentadienyl ring, in which the cyclopentadienyl ring or the fused ring containing a cyclopentadienyl ring may be further substituted by (C1-C20)alkyl, (C6-C30)aryl, (C2-C20)alkenyl or (C6-C30)ar(C1-C20)alkyl;

Ar represents (C6-C14)arylene;

$R^{11}$ and $R^{12}$ independently represent hydrogen atom, (C1-C10)alkyl or (C6-C13)aryl(C1-C10)alkyl;

n is an integer from 0 to 3; R represents (C1-C10)alkyl, (C3-C10)cycloalkyl, (C6-C13)aryl, (C1-C10)alkyl(C6-C13)aryl, (C6-C13)ar(C1-C10)alkyl or (C1-C10)alkoxy; when n is 2 or 3, individual substituents of R may be same or different;

$X^1$ and $X^2$ independently represent halogen atom, (C1-C20)alkyl, (C3-C20)cycloalkyl, (C6-C30)aryl, (C6-C30)ar(C1-C20)alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20)alkylthio, (C6-C30)arylthio, (C1-C20) alkylphosphine, (C6-C30)arylphosphine, (C1-C20)alkylmercapto or (C6-C30)arylmercapto;

the alkyl, cycloalkyl, aryl, arylalkyl, alkoxy, aryloxy, alkylsiloxy, arylsiloxy, alkylamino, arylamino, alkylthio, arylthio, alkylphosphine, arylphosphine, alkylmercapto, arylmercapto of R″, $X^1$ and $X^2$; and the arylene of Ar may be independently substituted by one or more substituent(s) selected from a group consisting of halogen, (C1-C10)alkyl, (C3-C20)cycloalkyl, (C6-C30)aryl, (C6-C30) ar (C1-C20) alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20)alkylthio, (C6-C30)arylthio, (C1-C20)alkylphosphine, (C6-C30)arylphosphine, (C1-C20)alkylmercapto and (C6-C30)arylmercapto; or each of them may be linked to an adjacent substituent via (C3-C12)alkylene or (C3-C12)alkenylene with or without a fused ring to form an alicyclic ring, or a monocyclic or polycyclic aromatic ring.

Another aspect of the invention to achieve the objects described above relates to catalyst composition comprising such transition metal compound and aluminoxane cocatalyst or boron compound cocatalyst.

Still another aspect of the invention to achieve the objects relates to processes for preparing ethylene homopolymers or copolymers of ethylene with α-olefins using the transition metal compound or the catalyst composition.

Now, the present invention is described in more detail.

The transition metal (M) of Group 4 in the Periodic Table of Elements in Chemical Formula (1) preferably represents titanium, zirconium or hafnium.

Cp represents a cyclopentadienyl ring which is $\eta^5$-linkable to the core metal, a cyclopentadiene ring with substituent(s), or a fused ring containing a cyclopentadienyl ring, such as indenyl or fluorenyl, with or without substituent(s). More specifically, examples of Cp include cyclopentadienyl, methyl cyclopentadienyl, dimethylcyclopentadienyl, tetramethylcyclopentadienyl, pentamethylcyclopentadienyl, butylcyclopentadienyl, sec-butylcyclopentadienyl, tert-butylmethylcyclopentadienyl, trimethylsilylcyclopentadienyl, indenyl, methylindenyl, dimethylindenyl, ethylindenyl, isopropylindenyl, fluorenyl, methylfluorenyl, dimethylfluorenyl, ethylfluorenyl, isopropylfluorenyl, and so on.

The group Ar may be (C6-C14)arylene such as phenylene, naphthalen-1-yl, naphthalen-2-yl, fluoren-2-yl and fluoren-4-yl. Among them, phenylene or naphthalen-2-yl are preferable.

Group R independently represents linear or non-linear (C1-C10)alkyl, such as methyl, ethyl, n-propyl, isopropyl, n-butyl, sec-butyl, tert-butyl, n-pentyl, neopentyl, tert-amyl, n-hexyl, n-octyl and tert-octyl, preferably methyl, ethyl, n-propyl, isopropyl, n-butyl, tert-butyl or tert-octyl; (C3-C10)cycloalkyl such as cyclohexyl; (C6-C13)aryl or (C1-C10)alkyl(C6-C13)aryl, such as phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, biphenyl and naphthyl, preferably phenyl, naphthyl, biphenyl, 2-isopropylphenyl, 3,5-xylyl or 2,4,6-trimethylphenyl; (C6-C13)aryl (C1-C10)alkyl such as benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl and (n-octylphenyl)methyl, preferably benzyl; (C1-C10)ar(C1-C10)alkyl such as benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (n-tetradecylphenyl)methyl, triphenylmethyl, naphthylmethyl or anthracenylmethyl, preferably benzyl or triphenylmethyl; or (C1-C10)alkoxy such as methoxy, ethoxy, n-propoxy, isopropoxy, n-butoxy, sec-butoxy, tert-butoxy, n-pentoxy, neopentoxy, n-hexoxy and n-octoxy, preferably methoxy or ethoxy.

Substituents $R^{11}$ and $R^{12}$ on the fluorenyl group of the ligand independently represent hydrogen atom, linear or non-linear (C1-C10)alkyl such as methyl, ethyl, n-propyl, isopropyl, n-butyl, isobutyl, n-pentyl, n-hexyl, n-octyl and 2-ethylhexyl, preferably methyl, ethyl, n-propyl, isopropyl, n-butyl, isobutyl, n-pentyl, n-hexyl or n-octyl; or (C6-C13)aryl(C1-C10)alkyl such as benzyl.

$X^1$ and $X^2$ independently represent halogen atom, (C1-C20)alkyl, (C3-C20)cycloalkyl, (C6-C30)aryl, (C6-C30)ar(C1-C20)alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20)alkylthio, (C6-C30)arylthio, (C1-C20)alkylphosphine, (C6-C30)arylphosphine, (C1-C20)alkylmercapto or (C6-C30)arylmercapto;

examples of halogen atom include fluorine, chlorine, bromine and iodine atoms; examples of (C1-C20)alkyl include methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl and n-eicosyl, preferably methyl, ethyl, isopropyl, tert-butyl or amyl; examples of (C3-C20) cycloalkyl include cyclopropane, cyclobutyl, cyclopentyl, cyclohexyl, cycloheptyl and adamantyl; examples of (C6-C30)aryl or (C6-C30)ar(C1-C20)alkyl include phenyl, naphthyl, fluorenyl, anthracenyl, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-tetradecylphenyl)methyl, naphthylmethyl and anthracenylmethyl, preferably benzyl;

examples of (C1-C20)alkoxy include methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy and n-eicocoxy, preferably methoxy, ethoxy, isopropoxy or tert-butoxy;

examples of (C6-C30)aryloxy include phenoxy, naphthalen-1-yloxy, naphthalen-2-yloxy, fluoren-2-yloxy and fluoren-4-yloxy, preferably phenoxy or fluoren-2-yloxy; examples of (C3-C20)alkylsiloxy include trimethylsiloxy, triethylsiloxy, tri-n-propylsiloxy, triisopropylsiloxy, tri-n-butylsiloxy, tri-sec-butylsiloxy, tri-tert-butylsiloxy, tri-isobutylsiloxy, tert-butyldimethylsiloxy, tri-n-pentylsiloxy, tri-n-hexylsiloxy and tricyclohexylsiloxy, preferably trimethylsiloxy or tert-butyldimethylsiloxy;

examples of amino groups having (C1-C20)alkyl or (C6-C30)aryl substituent(s) include dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, dibenzylamino, methylethylamino, methylphenylamino, benzylhexylamino, bistrimethylsilylamino and bis-tert-butyldimethylsilylamino;

examples of phosphines having (C1-C20)alkyl or (C6-C30)aryl substituent(s) include dimethylphosphine, diethylphosphine, di-n-propylphosphine, diisopropylphosphine, di-n-butylphosphine, di-sec-butylphosphine, di-tert-butylphosphine, diisobutylphosphine, tert-butylisopropylphosphine, di-n-hexylphosphine, di-n-octylphosphine, di-n-decylphosphine, diphenylphosphine, dibenzylphosphine, methylethylphosphine, methylphenylphosphine, benzylhexylphosphine, bistrimethylsilylphosphine and bis-tert-butyldimethylsilylphosphine, preferably dimethylphosphine, diethylphosphine or diphenylphosphine;

examples of mercapto groups having (C1-C20)alkyl or (C6-C30)aryl substituent(s) include methylmercapto, ethylmercapto, propylmercapto, isopropylmercapto, 1-butylmercapto and isopentylmercapto, phenylmercapto, naphthylmercapto and biphenylmercapto, preferably ethylmercapto or isopropylmercapto.

Examples of halogen, (C1-C20)alkyl, (C3-C20)cycloalkyl, (C6-C30)aryl, (C6-C30)ar(C1-C20)alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20)alkylthio, (C6-C30)arylthio, (C1-C20)alkylphosphine, (C6-C30)arylphosphine, (C1-C20)alkylmercapto or (C6-C30)arylmercapto to be further substituted on the alkyl, cycloalkyl, aryl, aralkyl, alkoxy, aryloxy, alkylsiloxy, arylsiloxy, alkylamino, arylamino, alkylthio, arylthio, alkylphosphine, arylphosphine, alkylmercapto or arylmercapto of $R''$, $X^1$ and $X^2$, or the arylene of Ar are described as above.

Examples of (C3-C12)alkylene for linkage of each substituent group to an adjacent substituent in order to form a ring with or without a fused ring include propylene, butylene, pentylene, hexylene, octylene, decylene and dodecylene, preferably butylene; and examples of (C3-C12)alkenylene include propenylene, butenylene, pentenylene, hexenylene, octenylene, decenylene and dodecenylene, preferably propenylene or butenylene.

Specifically, the present invention provides transition metal compounds selected from those represented by one of the following Chemical Formulas:

[Chemical Formula 1-1]

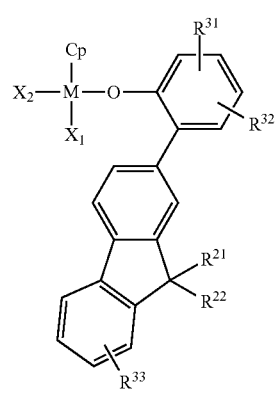

[Chemical Formula 1-2]

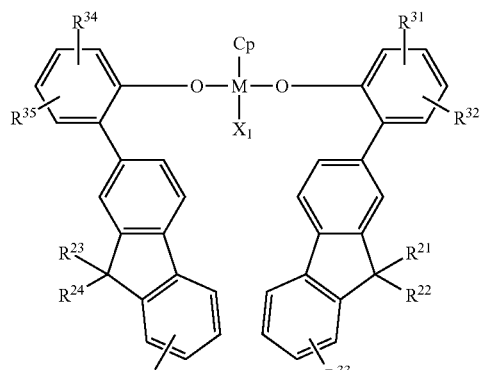

[Chemical Formula 1-3]

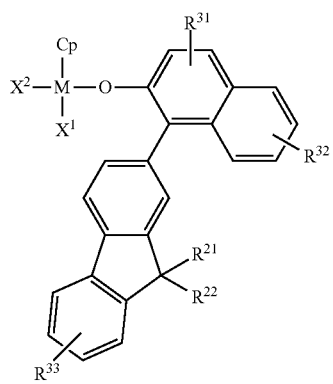

[Chemical Formula 1-4]

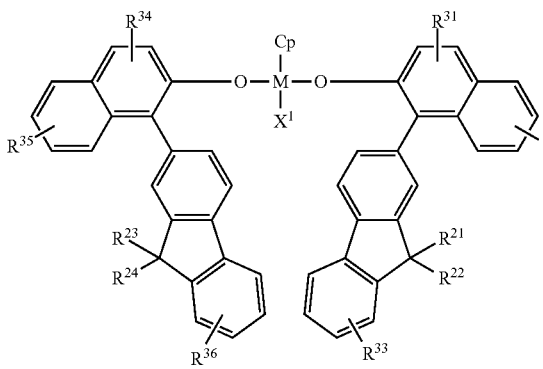

[Chemical Formula 1-5]

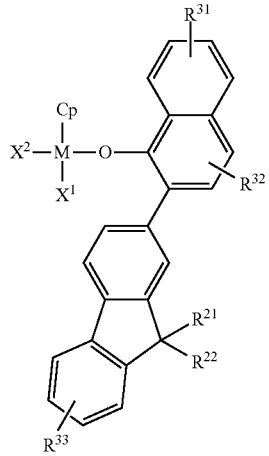

[Chemical Formula 1-6]

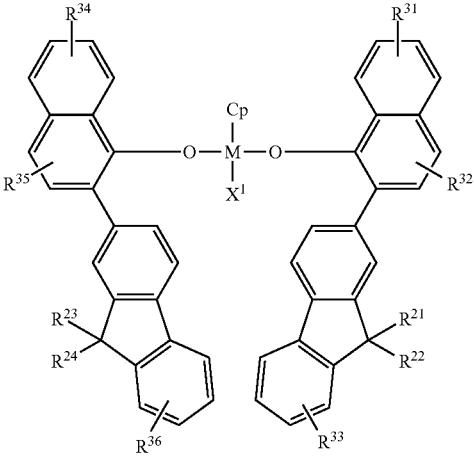

wherein, Cp represents cyclopentadienyl or pentamethylcyclopentadienyl;

M represents titanium, zirconium or hafnium;

$R^{21}$ through $R^{24}$ independently represent hydrogen or (C1-C10)alkyl;

$R^{31}$ through $R^{36}$ independently represent hydrogen atom, (C1-C10)alkyl, (C3-C10)cycloalkyl, (C6-C13)aryl, (C1-C10)alkyl(C6-C13)aryl, (C6-C13)ar(C1-C10)alkyl or (C1-C10)alkoxy;

$X^1$ and $X^2$ independently represent chloride, methyl, methoxy, isopropoxy, benzyl, fluorenyl, fluorenyloxy or dimethylamino.

More specifically, the transition metal compounds are characterized by being represented by one of the following Chemical Formulas:

1-1-1

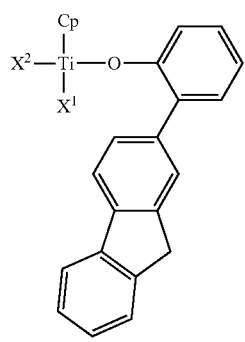

1-1-2

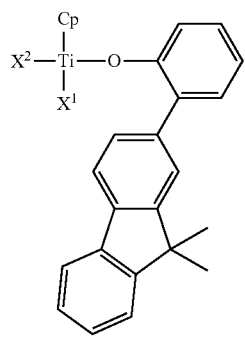

1-1-3
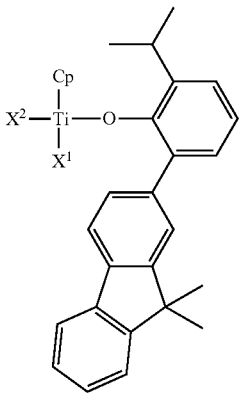
1-1-4
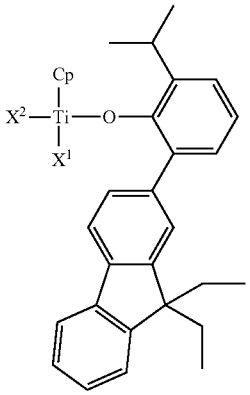
1-1-5
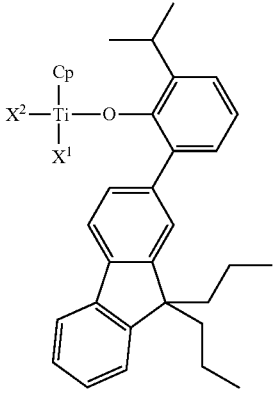
1-1-6
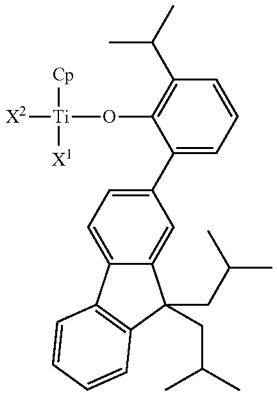
1-1-7
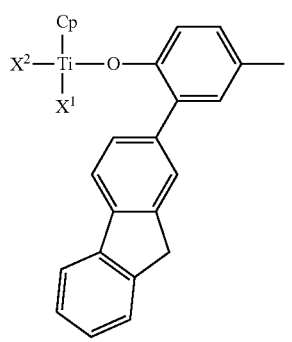
1-1-8
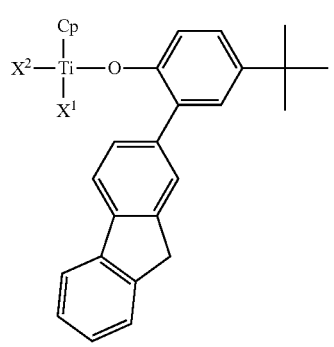
1-1-9
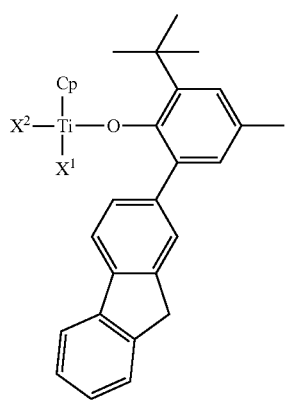
1-1-10
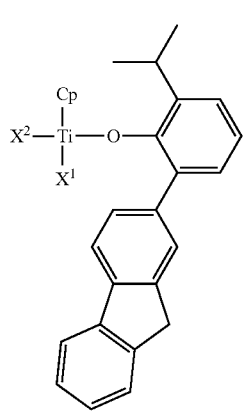

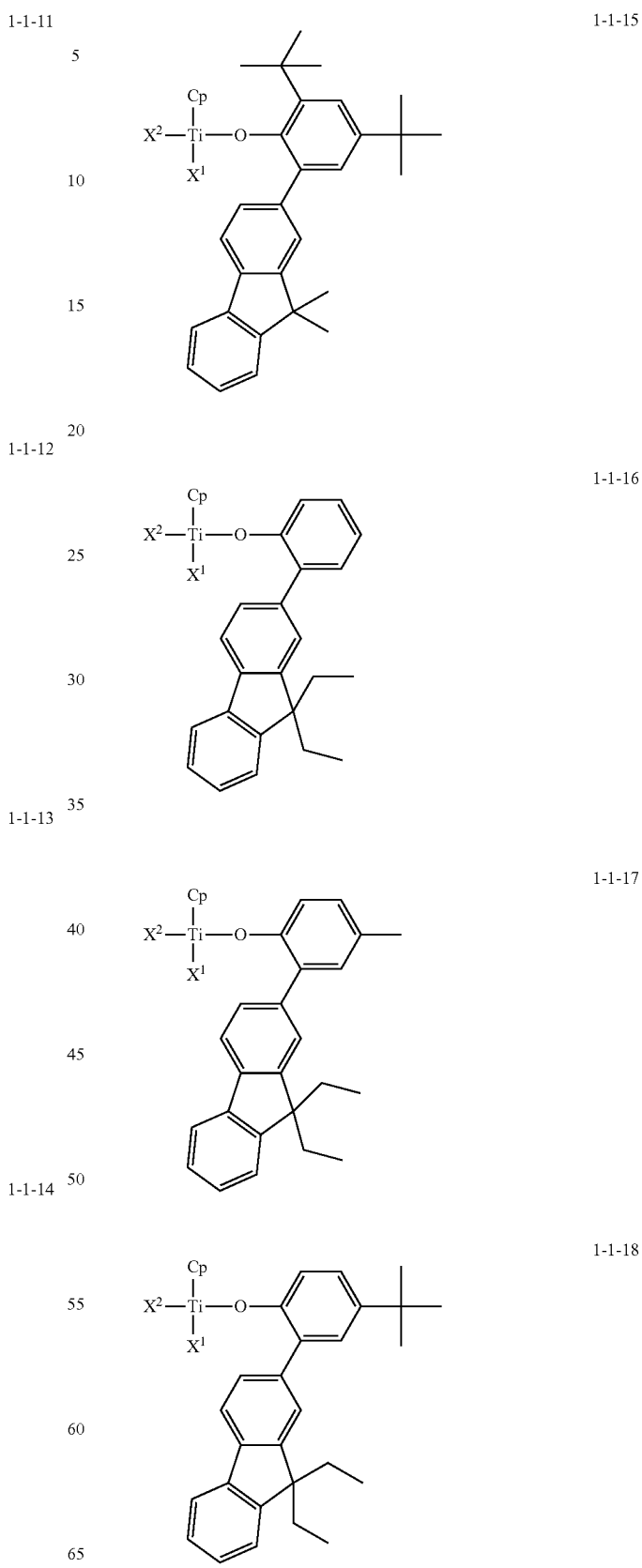

1-1-19 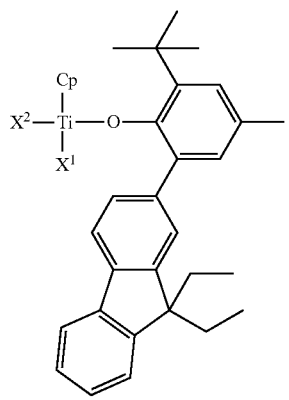
1-1-20 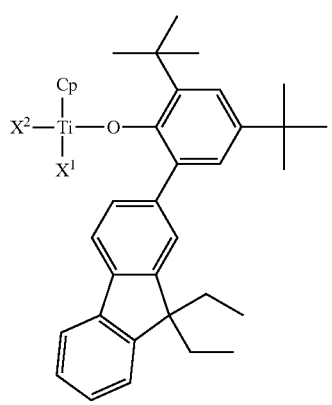
1-1-21 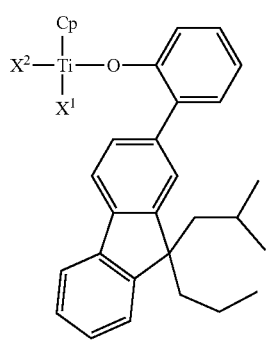
1-1-22 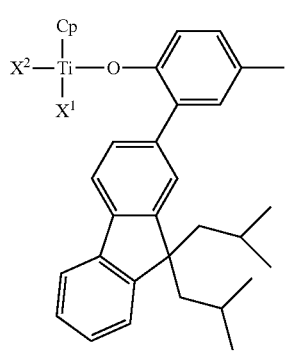
1-1-23 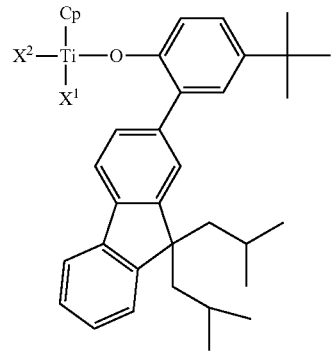
1-1-24 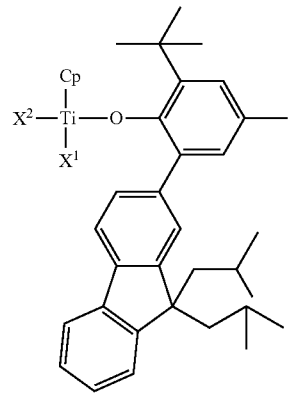
1-1-25 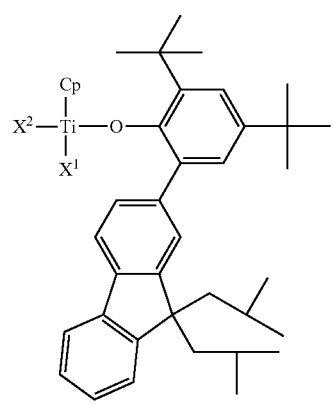
1-1-26 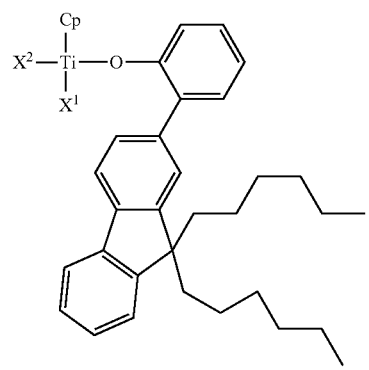

1-1-27
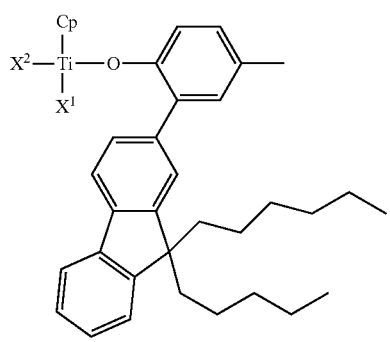
1-1-28
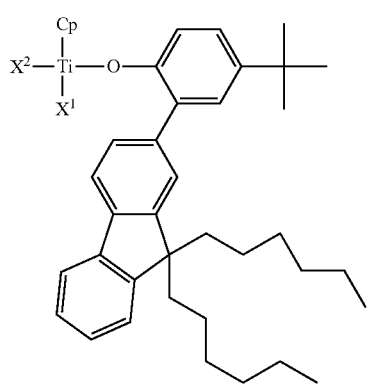
1-1-29
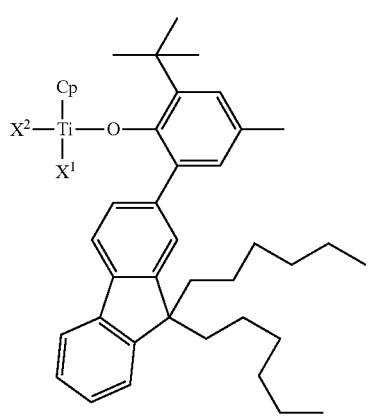
1-1-30
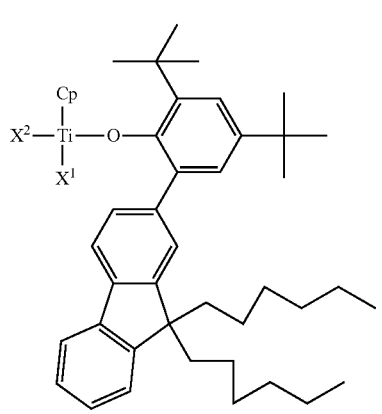
1-1-31
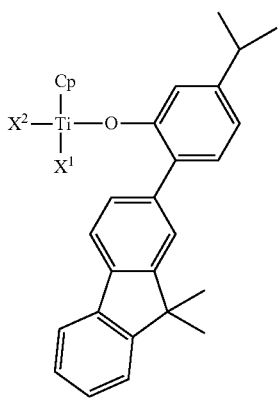
1-1-32
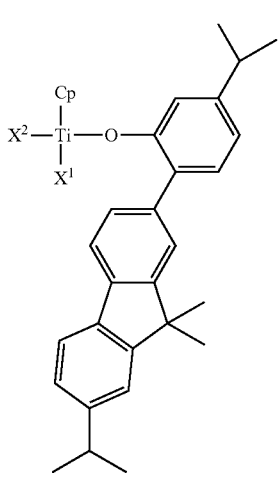
1-2-1
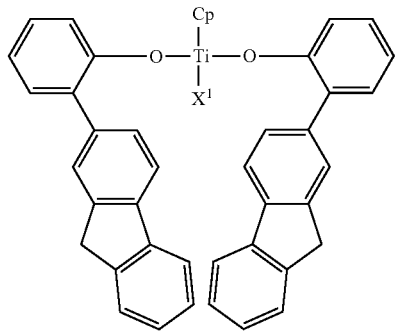
1-2-2
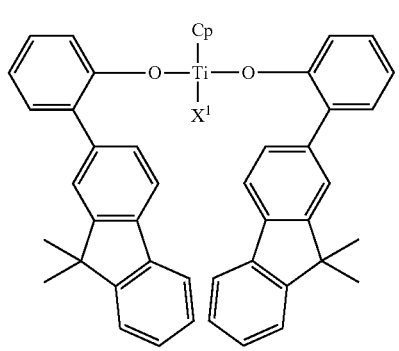

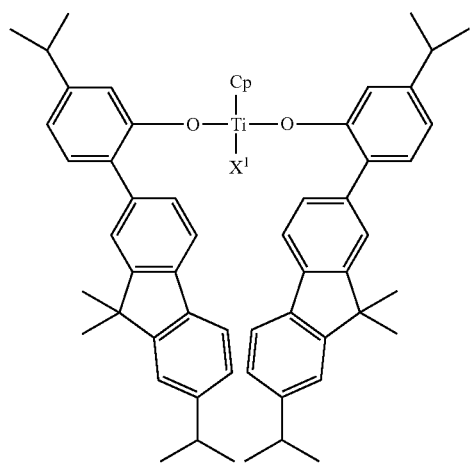
1-2-3
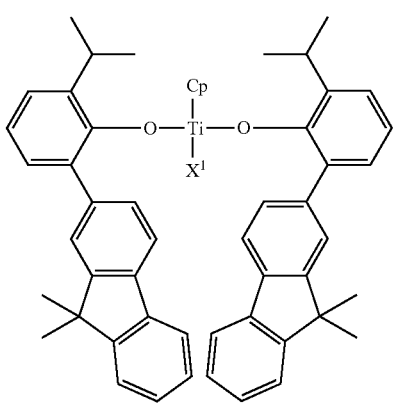
1-2-7
1-2-4
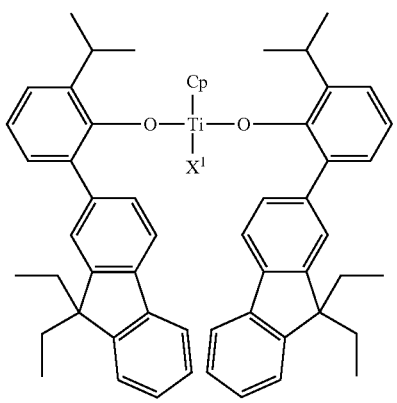
1-2-8
1-2-5
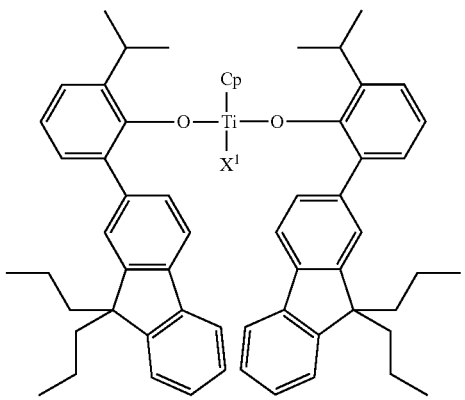
1-2-9
1-2-6
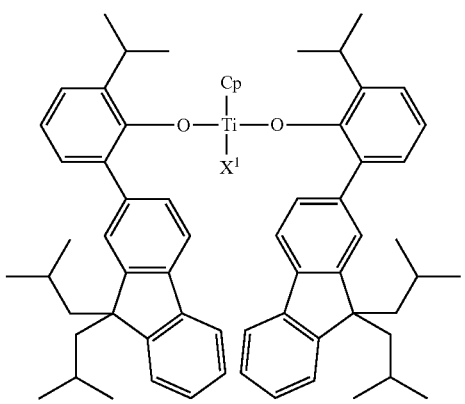
1-2-10

1-2-11
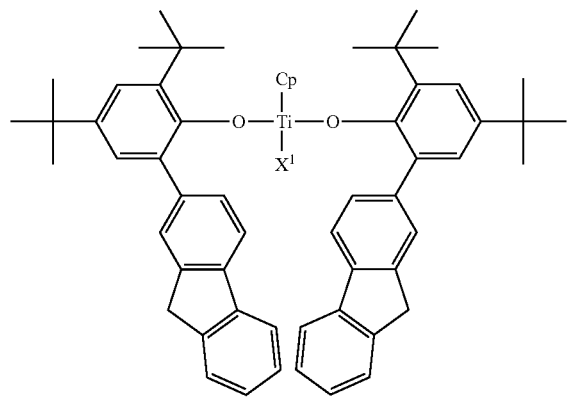
1-2-12
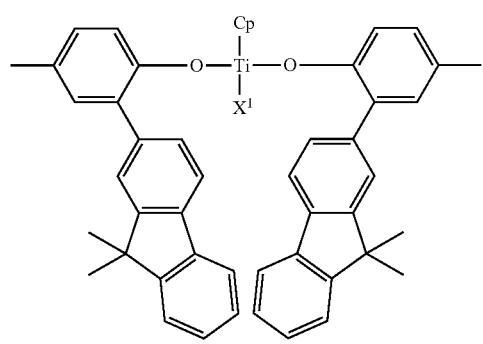
1-2-13
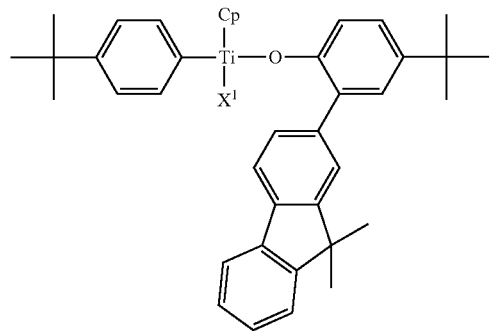
1-2-14
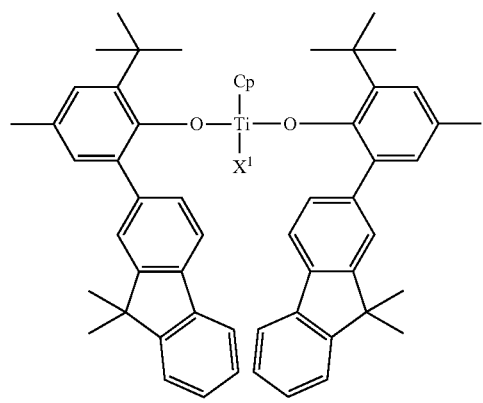
1-2-15
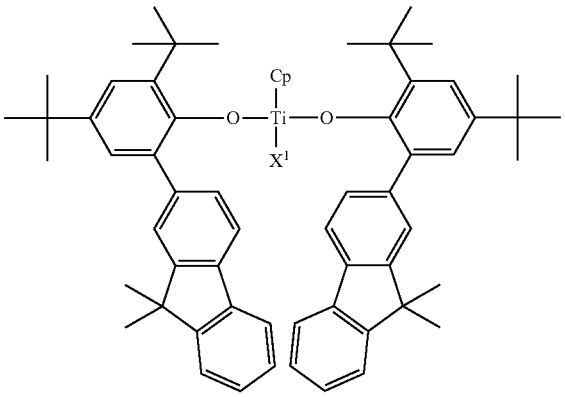
1-2-16
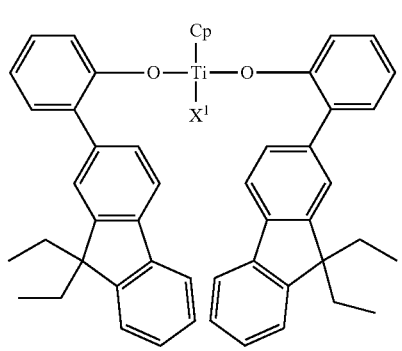
1-2-17
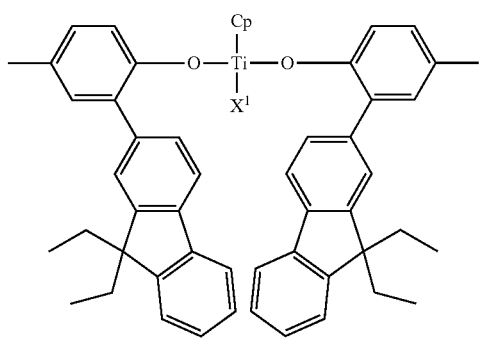
1-2-18
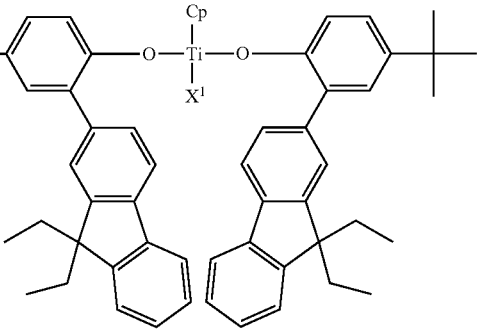

1-2-19
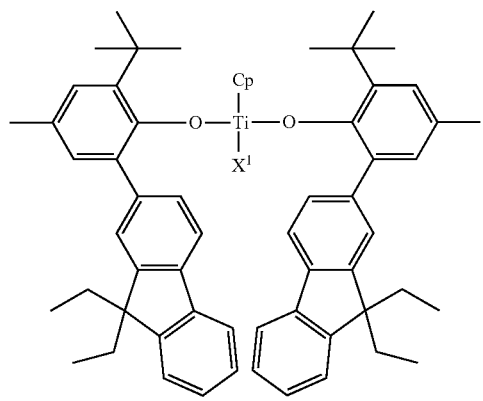
1-2-20
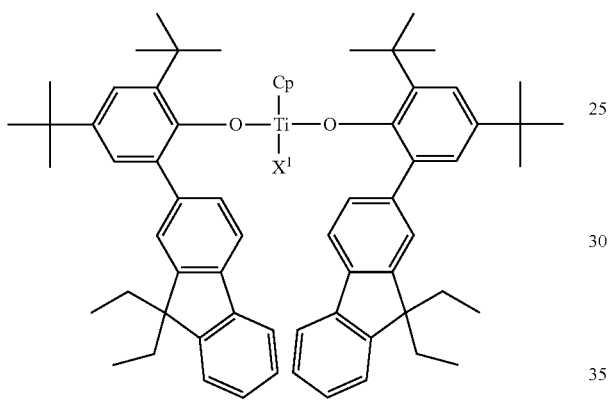
1-2-21
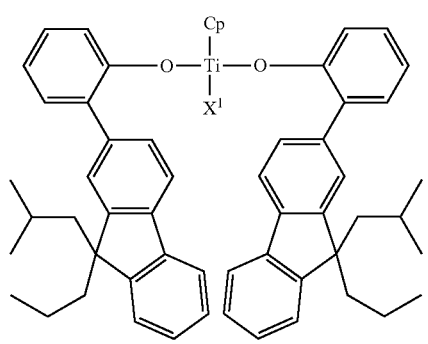
1-2-22
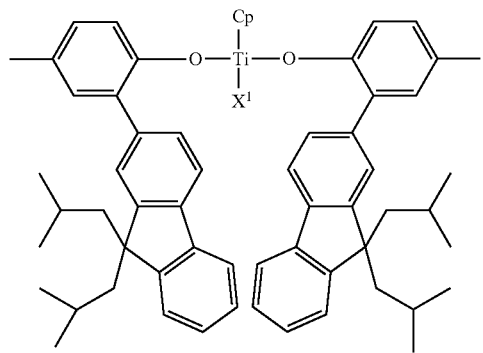
1-2-23
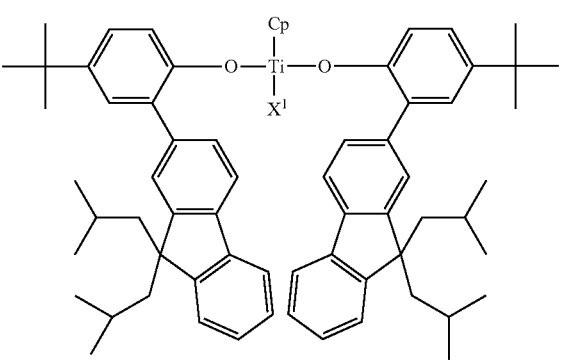
1-2-24
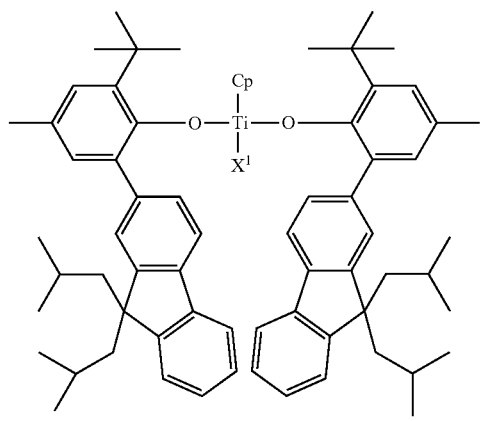
1-2-25
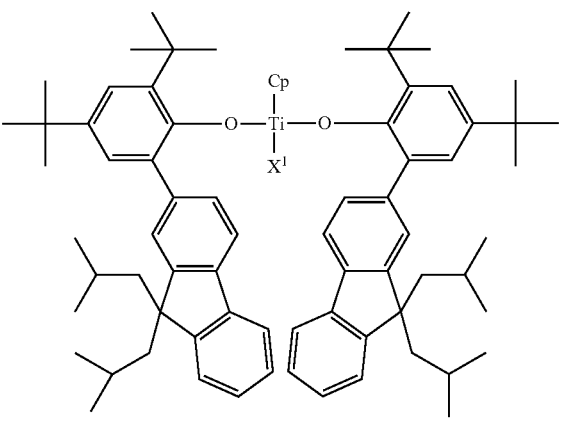

1-2-26
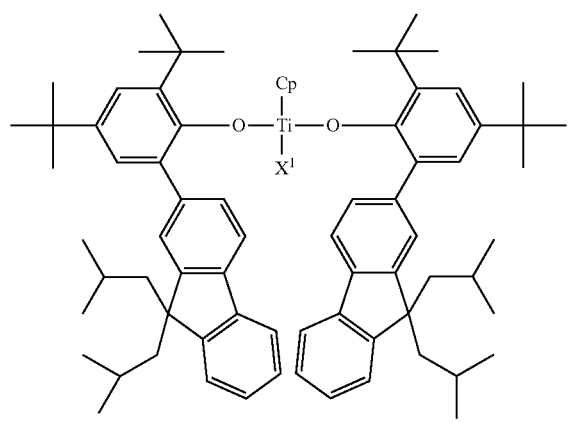
1-2-27
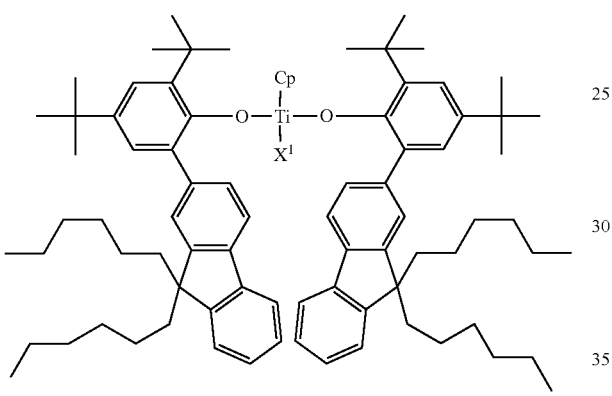
1-3-1
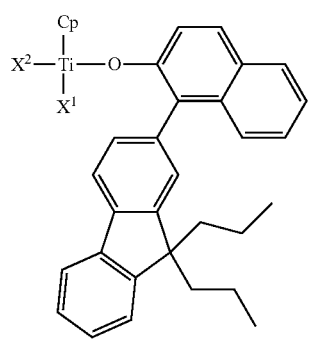
1-3-2
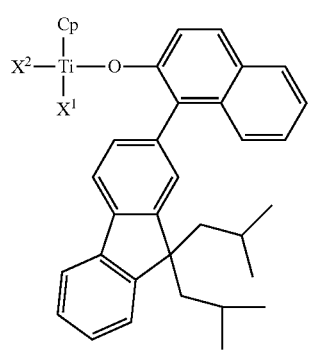
1-3-3
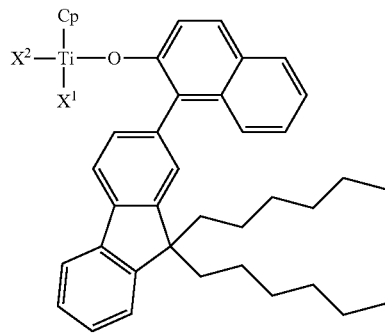
1-4-1
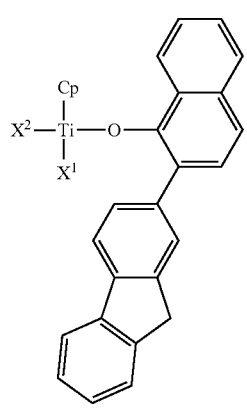
1-4-2
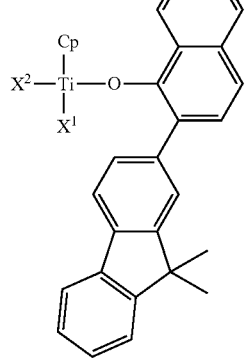
1-4-3
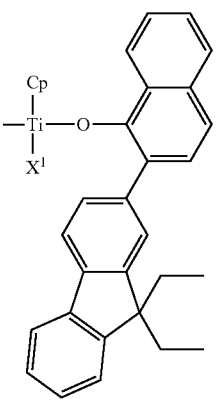

1-4-4
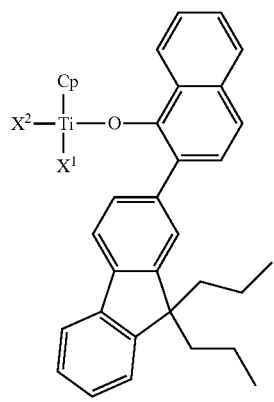
1-4-5
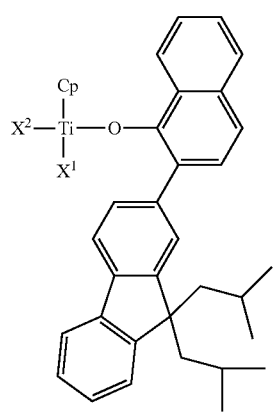
1-4-6
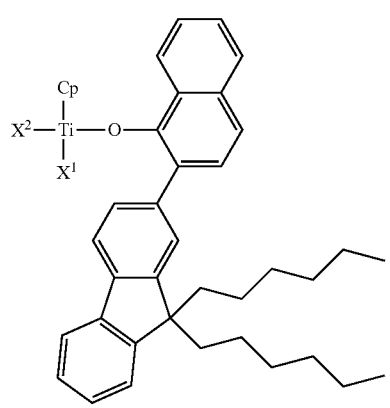
1-5-1
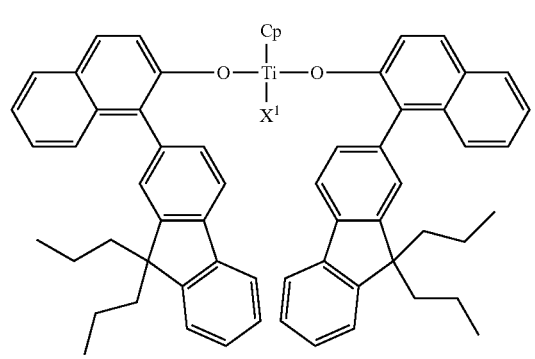
1-5-2
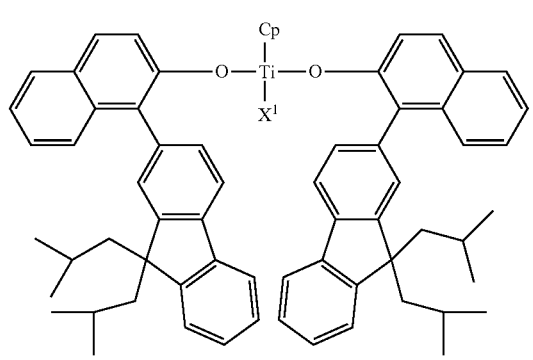
1-5-3
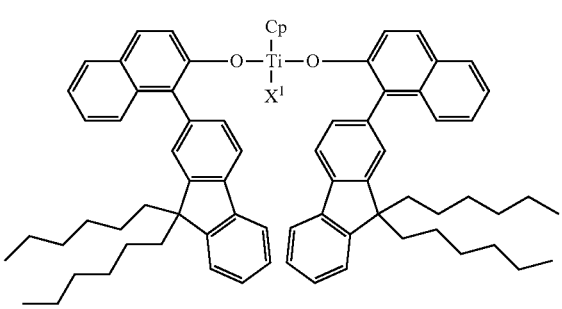
1-6-1
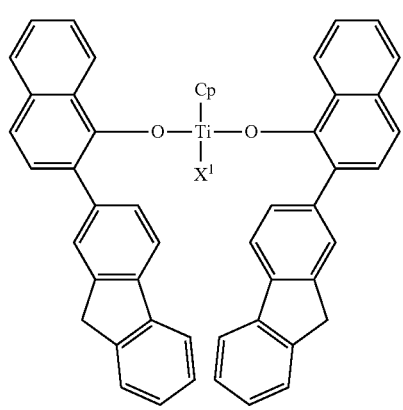
1-6-2
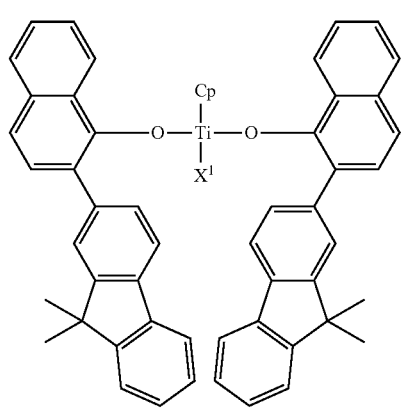

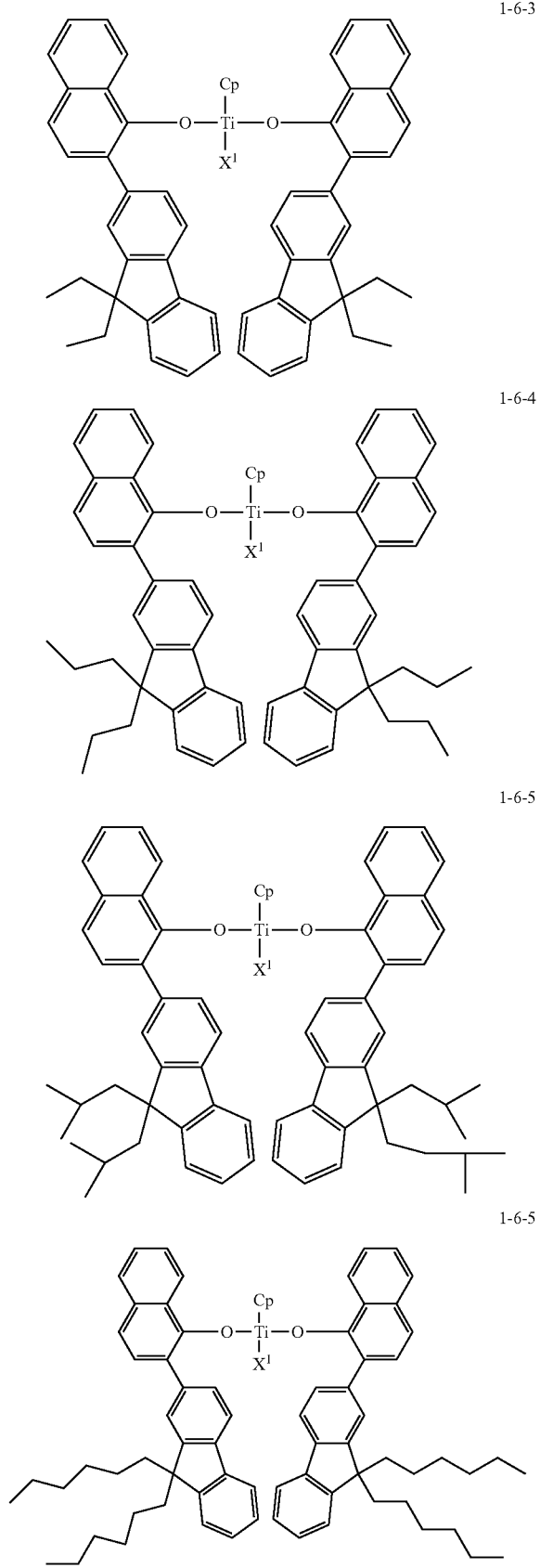

wherein, Cp represents cyclopentadienyl or pentamethylcyclopentadienyl; and $X^1$ and $X^2$ can be independently selected from a group consisting of chloride, methyl, methoxy, isopropoxy, benzyl, fluorenyl, fluorenyloxy and dimethylamino.

In the meanwhile, in order to provide active catalyst component to be used for preparing ethylene homopolymer or copolymer of ethylene with α-olefin, the transition metal compound represented by Chemical Formula (1) may be employed preferably with aluminoxane compound or boron compound, or a mixture thereof as cocatalyst, which can extract $X^1$ and $X^2$ ligands from the transition metal complex to cationize the core metal and act as a counterion (that is, an anion) having weak bond strength. The compositions comprising the transition metal compound and cocatalyst as described above fall under the scope of the present invention.

The boron compounds being usable as cocatalyst according to the present invention are disclosed in U.S. Pat. No. 5,198,401, and can be selected from the compounds represented by'one of Chemical Formulas (2) to (4):

$$B(R^{41})_3 \qquad \text{[Chemical Formula 2]}$$

$$[R^{42}]^+[B(R^{41})_4]^- \qquad \text{[Chemical Formula 3]}$$

$$[(R^{43})_pZH]^+[B(R^{41})_4]^- \qquad \text{[Chemical Formula 4]}$$

wherein, B represents boron atom; $R^{41}$ represents phenyl, which may be further substituted by three to five substituent(s) selected from fluorine, (C1-C20)alkyl with or without fluorine substituent(s) and (C1-C20)alkoxy with or without fluorine substituent(s); $R^{42}$ represents (C5-C7)aromatic radical or (C1-C20)alkyl(C6-C20)aryl radical, (C6-C30)aryl(C1-C20)alkyl radical such as triphenylmethyl radical; Z represents nitrogen or phosphorus atom; $R^{43}$ represents (C1-C20)alkyl radical, or anilinium radical having two (C1-C10)alkyl substituent(s) with nitrogen atom; and p is an integer of 2 or 3.

Preferable examples of the boron-containing cocatalyst include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl)borate, tetrakis(2,3,5,6-tetrafluorophenyl)borate, tetrakis(2,3,4,5-tetrafluorophenyl) borate, tetrakis(3,4,5-tetrafluorophenyl)borate, tetrakis(2,2,4-trifluorophenyl)borate, phenylbis(pentafluorophenyl) borate and tetrakis(3,5-bistrifluoromethylphenyl)borate. Certain compounded examples thereof include ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, triphenylmethyl tetrakis(3,5-bistrifluoromethylphenyl)borate, triethylammonium tetrakis (pentafluorophenyl)borate, tripropylammonium tetrakis (pentafluorophenyl)borate, tri(n-butyl)ammonium tetrakis (pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri (methylphenyl)phosphonium tetrakis(pentafluorophenyl)borate and tri(dimethylphenyl)phosphonium tetrakis(pentafluorophenyl)borate. Among them, preferable are N,N- dimethylanilinium tetrakispentafluorophenylborate, triphenylmethylinium tetrakispentafluorophenylborate and trispentafluoroborane.

The aluminium compounds being usable for the present invention include aluminoxane compounds represented by Chemical Formula (5) or (6), organoaluminum compounds represented by Chemical Formula (7), or organic aluminum hydrocarbyloxide compounds represented by Chemical Formula (8) or (9):

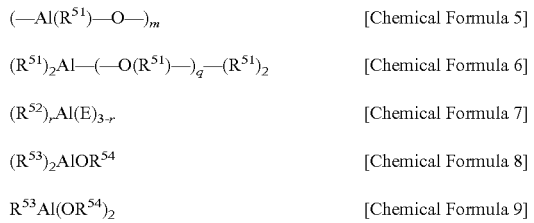

| | |
|---|---|
| $(-Al(R^{51})-O-)_m$ | [Chemical Formula 5] |
| $(R^{51})_2Al-(-O(R^{51})-)_q-(R^{51})_2$ | [Chemical Formula 6] |
| $(R^{52})_rAl(E)_{3-r}$ | [Chemical Formula 7] |
| $(R^{53})_2AlOR^{54}$ | [Chemical Formula 8] |
| $R^{53}Al(OR^{54})_2$ | [Chemical Formula 9] | wherein, $R^{51}$ represents (C1-C20)alkyl, preferably methyl or isobutyl; m and q independently are integers from 5 to 20; $R^{52}$ and $R^{53}$ independently represents (C1-C20) alkyl; E represents hydrogen or halogen atom; r is an integer from 1 to 3; and $R^{54}$ represents (C1-C20)alkyl or (C6-C30)aryl.

Specific examples of the aluminum compounds include aluminoxane compounds such as methylaluminoxane, modified methylaluminoxane, tetraisobutylaluminoxane; organic aluminum compounds such as trialkylaluminum including trimethylaluminum, triethylaluminum, tripropylaluminum, triisobutylaluminum and trihexylaluminum; dialkylaluminum chloride including dimethylaluminum chloride, diethylaluminum chloride, dipropylaluminum chloride, diisobutylaluminum chloride and dihexylaluminum chloride; alkylaluminum dichloride including methylaluminum dichloride, ethylaluminum dichloride, propylaluminum dichloride, isobutylaluminum dichloride and hexylaluminum dichloride; and dialkylaluminum hydride including dimethylaluminum hydride, diethylaluminum hydride, dipropylaluminum hydride, diisobutylaluminum hydride and dihexylaluminum hydride. Among them, preferable is trialkylaluminum, more preferable is triethylaluminum and triisobutylaluminum.

In the transition metal catalyst composition containing cocatalyst of the present invention for preparing ethylene homopolymers or copolymers of ethylene with α-olefin, ratio of the transition metal compound to the cocatalyst preferably ranges 1:0.1~100:10~1,000, more preferably 1:0.5~5:10~500 on the basis of the molar ratio of core metal: boron atom:aluminum atom.

According to another aspect of the present invention, the process for preparing ethylene polymers by using the transition metal catalyst composition is carried out by contacting the transition metal catalyst, cocatalyst and ethylene, and vinylic comonomer, if desired, in the presence of appropriate organic solvent. The transition metal catalyst and the cocatalyst component may be separately incorporated to the reactor, or those components may be previously mixed and charged to the reactor. The mixing conditions such as the order of feeding, temperature or concentration are not particularly restricted.

Preferable organic solvents to be employed for the process for preparation include (C3-C20)hydrocarbon, specifically, butane, isobutane, pentane, hexane, heptane, octane, isooctane, nonane, decane, dodecane, cyclohexane, methylcyclohexane, benzene, toluene and xylene.

Specifically, in the preparation of ethylene homopolymer, ethylene is used alone as the monomer. Appropriate pressure for the process according to the present invention is from 1 to 1000 atm, more preferably from 10 to 150 atm. The polymerization is effectively carried out at a temperature between 60° C. and 250° C., preferably between 80° C. and 200° C.

When preparing copolymers of ethylene and α-olefin, (C3-C18) α-olefin may be used as comonomer with ethylene. The comonomer may be preferably selected from a group consisting of propylene, 1-butene, 1-pentene, 4-methyl-1-pentene, 1-hexene, 1-octene, 1-decene, 1-dodecene, 1-hexadecene and 1-octadecene, more preferably from 1-butene, 1-hexene, 1-octene and 1-decene. Preferable ethylene pressure and temperature for polymerization are the same in case of preparing ethylene homopolymers. The copolymer prepared according to the process of the invention comprises at least 50% by weight, preferably at least 60% by weight, more preferably from 60 to 99% by weight of ethylene.

As described above, the linear low density polyethylene (LLDPE) prepared by using (C4-C10) α-olefin as the comonomer has density range of 0.910 to 0.940 g/cc. It is possible to extend the process up to the range of ultra low density polyethylene (VLDPE or ULDPE) or olefin elastomer of the density of 0.910 g/cc or lower. Upon preparing the ethylene homopolymers or copolymers thereof according to the invention, hydrogen may be employed as molecular weight modifier in order to adjust the molecular weight. The weight average molecular weight (Mw) of the polymers produced is usually from 80,000 to 500,000.

Since catalyst composition proposed by the present invention exists in homogeneous state in the polymerization reactor, it can be preferably applied to solution polymerization process carried out at a temperature higher than the melting point of the corresponding polymer. However, as disclosed by U.S. Pat. No. 4,752,597, the transition metal catalyst and cocatalyst may be supported by a carrier such as porous metal oxides, so that it can be used as heterogeneous catalyst composition for slurry polymerization or a gas phase polymerization process.

ADVANTAGEOUS EFFECTS

The transition metal compound according to the invention or the catalyst composition comprising the compound can be easily produced in a simple synthetic procedure with economic advantage. Due to its excellent thermal stability, the catalyst maintains high catalytic activity even at high temperature having high copolymerization reactivity with other olefins to result in polymers with high molecular weight with high yield.

BEST MODE

Hereinafter, the embodiments of the present invention will be described in detail with reference to accompanying Examples, which are not intended to restrict the scope of the invention.

Unless being stated otherwise, all experiments for synthesizing the ligands and catalysts were carried out under nitrogen atmosphere with standard Schlenk or glove-box technique, and the organic solvents were used after they had been dried via reflux over sodium metal and benzophenone, and then distilled immediately before use. ¹H-NMR analyses of the ligands and catalysts thus synthesized were performed by using Broker 500 MHz at ambient temperature.

As the solvent for polymerization, n-heptane was used after passing through a tube filled with molecular sieve 5A and activated alumina, and being bubbled by nitrogen with high purity to sufficiently remove moisture, oxygen and other catalyst poison. The polymers thus obtained were analyzed by the methods described below.

1. Melt Flow Index (MI)

MI was measured according to ASTM D 2839.

2. Density

Density was measured by using density gradient tube, according to ASTM D 1505.

3. Analysis of Melting Temperature (Tm)

Tm was measured under $2^{nd}$ heating condition at a rate of 10° C./min in the presence of nitrogen atmosphere, by means of Dupont DSC 2910.

4. Molecular Weight and Molecular Weight Distribution

Molecular weight was measured at 135° C. at a rate of 1.0 mL/min in the presence of 1,2,3-trichlorobenzene solvent by using PL210 GPC provided with PL Mixed-BX2+preCol. Molecular weight was calibrated by using PL polystyrene standards.

5. α-Olefin Content (wt %) in Copolymer

α-Olefin content was measured by means of Bruker DRX500 NMR spectroscope at 125 MHz by using 1,2,4-trichlorobenzene/$C_6D_6$ (7/3 by weight) mixed solvent at 120° C. in the $^{13}$C-NMR mode (reference: Randal, J. C. *JMS-Rev. Macromol. Chem. Phys.* 1980, C29, 201).

PREPARATION EXAMPLE 1

Synthesis of (dichloro) (pentamethylcyclopentadienyl) (2-(9',9"-dimethylfluoren-2'-yl)phenoxy)titanium(IV)

Synthesis of 2-bromo-9,9'-dimethylfluorene

A 1000 mL three-necked round bottomed flask was charged with 2-bromofluorene (25 g, 102.0 mmol), iodomethane (43.4 g, 306.0 mmol) and DMSO (300 mL), and the mixture was stirred under nitrogen atmosphere in order to obtain complete dissolution. Solution of potassium tert-butoxide (32.1 g, 285.6 mmol) dissolved in DMSO (400 mL) was slowly added dropwise thereto. The mixture was stirred at ambient temperature for 12 hours, and at 80° C. for 1 hour, and then cooled again to ambient temperature. The reaction mixture was mixed with water (1000 mL), and the resultant mixture was extracted with n-hexane. The organic layer was washed three times with distilled water, dried over magnesium sulfate ($MgSO_4$), and evaporated by using a rotary evaporator to remove solvent. Purification via silica gel column chromatography (eluent: n-hexane), and recrystallization again from n-hexane gave 2-bromo-9,9-dimethylfluorene (27.0 g, yield: 96.9%) as white solid.

$^1$H-NMR (CDCl$_3$) δ=1.65 (s, 6H), 7.35-7.39 (m, 2H), 7.44-7.50 (m, 2H), 7.58-7.62 (m, 2H), 7.72-7.73 (m, 1H) ppm Synthesis of 2-(2"-methoxyphenyl)-9,9'-dimethylfluorene To a flask charged with 2-bromo-9,9'-dimethylfluorene (27.0 g, 98.8 mmol), 2-methoxyphenylboronic acid (18.0 g, 118.6 mmol), palladium acetate (0.13 g, 0.6 mmol), triphenylphosphine (0.94 g, 3.6 mmol) and potassium phosphate (40.9 g, 177.9 mmol), added was mixture of water (70 mL) and dimethoxyethane (150 mL), and the resultant mixture was heated under reflux for 6 hours. After cooling the mixture to ambient temperature, aqueous ammonium chloride solution (150 mL) and diethyl ether (200 mL) were injected thereto. The organic layer was isolated, and the residue was extracted with diethyl ether. The combined organic layer was dried over magnesium sulfate and evaporated to remove the volatile substances. Purification via silica gel column chromatography (eluent: hexane) gave 2-(2"-methoxyphenyl-9,9'-dimethylfluorene (28.0 g, yield: 94.0%) as solid.

$^1$H-NMR (CDCl$_3$) δ=1.56 (s, 6H), 3.88 (s, 3H), 7.04-7.06 (d, 1H), 7.08-7.11 (t, 1H), 7.33-7.39 (m, 3H), 7.43-7.45 (d, 1H), 7.47-7.48 (d, 1H), 7.56-7.58 (d, 1H), 7.63 (s, 1H), 7.76-7.840 (t, 2H) ppm Synthesis of 2-(9',9"-dimethylfluoren-2'-yl)phenol To solution of 2-(2"-methoxyphenyl)-9,9'-dimethylfluorene (25.0 g, 83.2 mmol) in methylene chloride (400 mL), added dropwise was solution of boron tribromide (100 mL) (1M in methylene chloride) at −78° C., and the mixture reacted for three hours while slowly raising the temperature to ambient temperature. Then, mixture of ice (150 g) and diethyl ether (300 mL) was added thereto. The organic layer was isolated, and the aqueous layer was extracted with diethyl ether. The combined organic layer was dried over magnesium sulfate and evaporated to remove the volatile substances. Purification via silica gel column chromatography (eluent: mixture of hexane and methylene chloride) gave 2-(9',9"-dimethylfluoren-2'-yl)phenol (18.0 g, yield: 75.5%) as white solid.

$^1$H-NMR (CDCl$_3$) δ=1.55 (s, 6H), 7.04-7.07 (m, 2H), 7.30-7.40 (m, 4H), 7.47-7.50 (m, 2H), 7.55 (s, 1H), 7.78-7.80 (d, 1H), 7.85-7.87 (d, 1H) ppm Synthesis of (dichloro) (pentamethylcyclopentadienyl)(2-(9',9"-dimethylfluoren-2'-yl)phenoxy)titanium(IV)

To solution of 2-(9',9"-dimethylfluoren-2'-yl)phenol (5.0 g, 17.1 mmol) in toluene (200 mL), slowly injected was n-butyllithium (2.5 M in hexane, 6.9 mL) at −78° C., and the mixture was stirred at ambient temperature for 12 hours. After chilling the reaction mixture to −78° C., slowly added was solution of (pentamethylcyclopentadienyl)titanium(IV) trichloride (4.7 g, 16.3 mmol) in toluene (100 mL), and the reaction was carried out at ambient temperature for 12 hours. When the reaction was completed, the reaction mixture was filtered through a celite filter, and solvent was removed therefrom. Recrystallization was carried out from purified toluene and hexane at −35° C. The solid was filtered and dried under reduced pressure to obtain (dichloro)(pentamethylcyclopentadienyl)(2-(9',9"-dimethylfluoren-2'-yl)phenoxy)titanium(IV) (5.6 g, yield: 63.9%) as red solid.

$^1$H-NMR ($C_6D_6$) δ=1.61 (s, 6H), 1.77 (s, 15H), 7.03-7.05 (t, 1H), 7.16-7.19 (t, 1H), 7.32-7.34 (m, 2H), 7.37-7.39 (d, 1H), 7.42-7.44 (d, 1H), 7.46-7.47 (d, 1H), 7.71-7.77 (m, 3H), 7.82-7.84 (d, 1H) ppm Mass (APCI mode, m/z): 539.4

PREPARATION EXAMPLE 2

Synthesis of (chloro)(pentamethylcyclopentadienyl) (bis(2-(9',9"-dimethylfluoren-2'-yl)phenoxy))titanium(IV)

To solution of 2-(9',9"-dimethylfluoren-2'-yl)phenol (5.0 g, 17.1 mmol) in toluene (200 ml), slowly injected was n-butyllithium (2.5 M in hexane, 6.9 mL) at −78° C., and the mixture was stirred at ambient temperature for 12 hours. After chilling the reaction mixture to −78° C., slowly added was solution of (pentamethylcyclopentadienyl)titanium(IV) trichloride (2.3 g, 8.0 mmol) in toluene (100 mL), and the reaction was carried out at 80° C. for 12 hours. When the reaction was completed, the reaction mixture was filtered through a celite filter, and solvent was removed therefrom. Recrystallization was carried out from purified toluene and hexane at −35° C. The solid was filtered and dried under reduced pressure to obtain (chloro)(pentamethylcyclopentadienyl)(bis(2-(9',9"-dimethylfluoren-2'-yl)phenoxy)titanium (IV) (3.5 g, yield: 55.8%) as orange solid.

$^1$H-NMR (C$_6$D$_6$) δ=1.54 (s, 6H), 1.61 (s, 6H), 1.65 (s, 15H), 7.01-7.04 (t, 2H), 7.21-7.24 (t, 2H), 7.33-7.36 (m, 4H), 7.39-7.41 (t, 4H), 7.44-7.46 (m, 2H), 7.65 (s, 2H), 7.73-7.757 (t, 2H), 7.82-7.88 (m, 4H) ppm Mass (APCI mode, m/z): 789.3

PREPARATION EXAMPLE 3

Synthesis of (dichloro)(pentamethylcyclopentadienyl)(2-(9'H-fluoren-2'-yl)phenoxy)titanium(IV)

Synthesis of 2-(2'-methoxyphenyl)-9H-dimethylfluorene

To a flask charged with 2-bromo-9H-fluorene (10.0 g, 40.8 mmol), 2-methoxyphenylboronic acid (7.4 g, 49.0 mmol), palladium acetate (0.055 g, 0.245 mmol), triphenylphosphine (0.44 g, 1.4 mmol) and potassium phosphate (2.0 g, 95.5 mmol), added was mixture of water (33 mL) and dimethoxyethane (100 mL), and the resultant mixture was heated under reflux for 6 hours. After cooling the mixture to ambient temperature, aqueous ammonium chloride solution (100 mL) and diethyl ether (150 mL) were injected thereto. The organic layer was isolated, and the residue was extracted with diethyl ether. The combined organic layer was dried over magnesium sulfate and evaporated to remove the volatile substances. Purification via silica gel column chromatography (eluent: hexane) gave 2-(2'-methoxyphenyl-9H-dimethylfluorene (10.0 g, yield: 90.0%) as solid.

$^1$H-NMR (CDCl$_3$) δ=3.87 (s, 3H), 3.98 (s, 2H), 7.04-7.05 (d, 1H), 7.07-7.10 (t, 1H), 7.32-7.42 (m, 4H), 7.57-7.59 (d, 2H), 7.74 (s, 1H), 7.83-7.86 (t, 2H) ppm Synthesis of 2-(9'H-fluoren-2'-yl)phenol To solution of 2-(2'-methoxyphenyl)-9H-dimethylfluorene (10.0 g, 36.7 mmol) in methylene chloride (200 mL), added dropwise was solution of boron tribromide (44 ml) (1M in methylene chloride) at −78° C., and the mixture reacted for three hours while slowly raising the temperature to ambient temperature. Then, mixture of ice (150 g) and diethyl ether (200 mL) was added thereto. The organic layer was isolated, and the aqueous layer was extracted with diethyl ether. The combined organic layer was dried over magnesium sulfate and evaporated to remove the volatile substances. Purification via silica gel column chromatography (eluent: mixture of hexane and methylene chloride) gave 2-(9'H-fluoren-2'-yl) phenol (7.0 g, yield: 73.8%) as white product.

$^1$H-NMR (CDCl$_3$) δ=3.96 (s, 2H), 7.00-7.02 (m, 2H), 7.25-7.35 (m, 3H), 7.39-7.42 (t, 1H), 7.47-7.49 (d, 1H), 7.56-7.58 (d, 1H), 7.64 (s, 1H), 7.81-7.83 (d, 1H), 7.88-7.89 (d, 1H) ppm Synthesis of (dichloro)(pentamethylcyclopentadienyl)(2-(9'H-fluoren-2'-yl)phenoxy)titanium(IV)

To solution of 2-(9'H-fluoren-2'-yl)phenol (4.4 g, 17.0 mmol) in toluene (200 mL), slowly injected was n-butyllithium (2.5 M in hexane, 6.9 mL) at −78° C., and the mixture was stirred at ambient temperature for 12 hours. After chilling the reaction mixture to −78° C., slowly added was solution of (pentamethylcyclopentadienyl)titanium(IV) trichloride (4.7 g, 16.3 mmol) in toluene (100 mL), and the reaction was carried out at ambient temperature for 12 hours. When the reaction was completed, the reaction mixture was filtered through a celite filter, and solvent was removed therefrom. Recrystallization was carried out from purified toluene and hexane at −35° C. The solid was filtered and dried under reduced pressure to obtain (dichloro)(pentamethylcyclopentadienyl)(2-(9'H-fluoren-2'-yl)phenoxy)titanium(IV) (5.6 g, yield: 71.0%) as red solid.

$^1$H-NMR (C$_6$D$_6$) δ=1.72 (s, 15H), 3.94 (s, 2H), 7.05-7.18 (m, 2H), 7.36-7.38 (m, 2H), 7.44-7.46 (m, 2H), 7.48-7.50 (d, 1H), 7.65-7.66 (d, 1H), 7.81-7.82 (d, 1H), 7.86-7.87 (d, 1H), 7.98 (1, 1H) ppm Mass (APCI mode, m/z): 511.3

PREPARATION EXAMPLE 4

Synthesis of (dichloro)(pentamethylcyclopentadienyl)(2-tert-butyl-6-(9',9"-dimethylfluoren-2'-yl)-4-methylphenoxy)titanium(IV)

Synthesis of 9',9"-dimethylfluoren-2'-yl boronic acid

In a 500 mL three-necked round-bottomed flask, 2-bromofluorene (30 g, 105.1 mmol) was dissolved in THF (250 mL), and n-butyllithium (2.5 M solution in hexane) (44.1 mL, 110.4 mmol) was slowly added dropwise thereto at −78° C. under nitrogen atmosphere. After stirring at ambient temperature, the mixture was chilled to −78° C., and triethyl borate (22.8, 157.7 mmol) was slowly added dropwise thereto. The mixture was then stirred at ambient temperature for 12 hours, and poured into mixture of 2N aqueous hydrochloric acid (300 mL) and ice (300 g). After stirring for 2 hours, the mixture was extracted with diethyl ether. The organic layer was washed three times with distilled water, dried over anhydrous magnesium sulfate (MgSO$_4$), and evaporated by using a rotary evaporator to remove solvent. Recrystallization from n-hexane and ethyl acetate (10:1) gave 9',9"-dimethylfluoren-2'-ylboronic acid (16.0 g, yield: 64.0%) as white product.

$^1$H-NMR (CDCl$_3$) δ=1.71 (s, 6H), 7.43-7.57 (m, 3H), 7.88-7.96 (m, 2H), 8.39-8.40 (m, 2H) ppm Synthesis of 1-bromo-3-tert-butyl-2-methoxy-5-methylbenzene A 500 mL three-necked round-bottomed flask was charged with 2-bromo-6-tert-butyl-4-methylphenol (20.0 g, 82.3 mmol), potassium hydroxide (9.7 g, 164.5 mmol) and DMSO (dimethylsulfoxide) (100 mL), and the mixture was chilled to 0° C. After slowly injecting iodomethane (23.4 g, 164.5 mmol) thereto, the resultant mixture was stirred at ambient temperature for 12 hours. The reaction mixture was then poured into ice (200 g), and the resultant mixture stirred for 30 minutes. After adding diethyl ether, the organic layer was isolated and the residue was extracted with diethyl ether. The combined organic layer was dried over magnesium sulfate, and evaporated to remove volatiles. Recrystallization from mixture of hexane and dichloromethane gave 1-bromo-3-tert-butyl-2-methoxy-5-methylbenzene (17.5 g, yield: 82.8%).

$^1$H-NMR (CDCl$_3$) δ=1.41 (s, 9H), 2.38 (s, 3H), 3.82 (s, 3H), 7.04 (s, 1H), 7.13 (s, 1H) ppm Synthesis of 2-(3-tert-butyl-2-methoxy-5-methylphenyl)-9',9"-dimethylfluorene To a flask charged with 1-bromo-3-tert-butyl-2-methoxy-5-methylbenzene (9.0 g, 35.0 mmol), 9',9"-dimethylfluoren- 2'-ylboronic acid (10.0 g, 42.0 mmol), palladium acetate (0.024 g, 0.105 mmol), o-triphenylphosphine (0.19 g, 0.63 mmol) and potassium phosphate (14.5 g, 63.0 mmol), added was mixture of water (25 mL) and dimethoxyethane (150 mL), and the resultant mixture was heated under reflux for 6 hours. After cooling the mixture to ambient temperature, aqueous ammonium chloride solution (100 mL) and diethyl ether (150 mL) were injected thereto. The organic layer was isolated, and the residue was extracted with diethyl ether. The combined organic layer was dried over magnesium sulfate and evaporated to remove the volatile substances. Purification via silica gel column chromatography (eluent: hexane) gave 3-tert-butyl-2-methoxy-5-methylphenyl-9',9''-dimethylfluorene (12.0 g, yield: 93.0%) as solid.

$^1$H-NMR (CDCl$_3$) δ=1.47 (s, 9H), 1.56 (s, 6H), 2.30 (s, 3H), 3.90 (s, 3H), 6.89 (S, 1H), 7.23 (s, 1H), 7.36-7.41 (m, 3H), 7.46-7.50 (m, 2H), 7.78-7.81 (m, 2H) ppm

Synthesis of 2-tert-butyl-6-(9',9''-dimethylfluoren-2'-yl)-4-methylphenol

To solution of 3-tert-butyl-2-methoxy-5-methylphenyl)-9',9''-dimethylfluorene (22.0 g, 73.2 mmol) in methylene chloride (500 mL), added dropwise was solution of boron tribromide (88 mL) (1M in methylene chloride) at −78° C., and the mixture reacted for three hours while slowly raising the temperature to ambient temperature. Then, mixture of ice (200 g) and diethyl ether (300 mL) was added thereto. The organic layer was isolated, and the aqueous layer was extracted with diethyl ether. The combined organic layer was dried over magnesium sulfate and evaporated to remove the volatile substances. Purification via silica gel column chromatography (eluent: mixture of hexane and methylene chloride) gave 2-tert-butyl-6-(9',9''-dimethylfluoren-2'-yl)-4-methylphenol (18.0 g, yield: 85.9%) as white solid.

$^1$H-NMR (CDCl$_3$) δ=1.53 (s, 9H), 1.60 (s, 6H), 2.23 (s, 3H), 4.70 (s, 1H (—OH)), 6.69 (s, 1H), 7.32-7.40 (m, 4H), 7.42 (s, 1H), 7.47-7.49 (d, 1H), 7.77-7.78 (d, 1H) ppm

Synthesis of (dichloro) (pentamethylcyclopentadienyl)(2-tert-butyl-6-(9',9''-dimethylfluoren-2'-yl)-4-methylphenoxy)titanium(IV)

To solution of 2-tert-butyl-6-(9',9''-dimethylfluoren-2'-yl)-4-methylphenol (5.0 g, 14.0 mmol) in toluene (200 ml), slowly injected was n-butyllithium (2.5 M in hexane, 5.6 mL) at −78° C., and the mixture was stirred at ambient temperature for 12 hours. After chilling the reaction mixture to −78° C., slowly added was solution of (pentamethylcyclopentadienyl) titanium(IV) trichloride (4.7 g, 13.3 mmol) in toluene (100 mL), and the reaction was carried out at ambient temperature for 12 hours. When the reaction was completed, the reaction mixture was filtered through a celite filter, and solvent was removed therefrom. Recrystallization was carried out from purified toluene and hexane at −35° C. The solid was filtered and dried under reduced pressure to obtain (dichloro)(pentamethylcyclopentadienyl)(2-tert-butyl-6-(9',9''-dimethylfluoren-2'-yl)-4-methylphenoxy)titanium(IV) (5.5 g, yield: 66.7%) as red solid.

$^1$H-NMR (C$_6$D$_6$) δ=1.51 (s, 6H), 1.70 (s, 9H), 2.10 (s, 15H), 2.42 (s, 3H), 7.30-7.39 (m, 5H), 7.50-7.52 (d, 1H), 7.59-7.60 (s, 1H), 7.73-7.77 (m, 2H) ppm Mass (APCI mode, m/z): 609.5

EXAMPLE 1

In a batch-type polymerization reactor, copolymerization of ethylene with 1-octene was carried out as described below.

In a 2000 mL stainless steel reactor, which had been sufficiently dried and purged with nitrogen, charged was cyclohexane (1140 mL) and 1-octene (60 mL). Then, 54.2 mM solution (11.1 mL) of modified methylaluminoxane-7 (modified MAO-7, 7 wt % Al Isopar solution, from Akzo Nobel) in toluene was added thereto. Then, the temperature of the reactor was raised to 140° C., and (dichloro)(pentamethylcyclopentadienyl)(2-(9',9''-dimethylfluoren-2'-yl)phenoxy)titanium(IV) (5 mM solution in toluene) (0.4 mL) which had been synthesized from Preparation Example 1 and 10 mM solution of triphenylmethylinium tetrakispentafluorophenylborate (99%, Boulder Scientific) in toluene (0.6 mL) were sequentially added thereto. By means of ethylene, the pressure in the reactor was then made up to 30 kg/cm$^2$, with continual supply thereof to carry out polymerization. In one minute of the reaction, maximum temperature 176° C. was achieved. After 1 minute, 100 mL of ethanol containing 10 vol % of aqueous hydrochloric acid was added to quench the polymerization. Then, the mixture was stirred with 1.5 L of ethanol for 1 hour, and the reaction product was filtered and isolated. The reaction product thus collected was dried in an vacuum oven at 60° C. for hours to obtain 45.9 g of polymer. The polymer had the melting point of 90.3° C., melt index of 17.3 and density of 0.8932 g/cc. As the result of analysis via gel chromatography, the polymer had weight average molecular weight (Mw) of 47,400 g/mol, molecular weight distribution (Mw/Mn) of 2.71, and 1-octene content of 18.5% by weight.

EXAMPLE 2

In a batch-type polymerization reactor, copolymerization of ethylene with 1-octene was carried out as described below.

In a 2000 mL stainless steel reactor, which had been sufficiently dried and purged with nitrogen, charged was cyclohexane (1140 mL) and 1-octene (60 mL). Then, 54.2 mM solution (11.1 mL) of modified methylaluminoxane-7 (modified MAO-7, 7 wt % Al Isopar solution, from Akzo Nobel) in toluene was added thereto. Then, the temperature of the reactor was raised to 140° C., and (chloro) (pentamethylcyclopentadienyl)(bis(2-(9',9''-dimethylfluoren-2'-yl)phenoxy)) titanium(IV) (5 mM solution in toluene) (0.4 mL) which had been synthesized from Preparation Example 2 and 10.0 mM solution of triphenylmethylinium tetrakispentafluorophenylborate (99%, Boulder Scientific) in toluene (0.6 mL) were sequentially added thereto. By means of ethylene, the pressure in the reactor was then made up to 30 kg/cm$^2$, with continual supply thereof to carry out polymerization. In one minute of the reaction, maximum temperature 1° C. was achieved. After 1 minute, 100 mL of ethanol containing 10 vol % of aqueous hydrochloric acid was added to quench the polymerization. Then, the mixture was stirred with 1.5 L of ethanol for 1 hour, and the reaction product was filtered and isolated. The reaction product thus collected was dried in an vacuum oven at 60° C. for 8 hours to obtain 38.0 g of polymer. The polymer had the melting point of 91.5° C., melt index of 22.0 and density of 0.8944 g/cc. As the result of analysis via gel chromatography, the polymer had weight average molecular weight (Mw) of 51,200 g/mol, molecular weight distribution (Mw/Mn) of 2.26, and 1-octene content of 17.9% by weight.

EXAMPLE 3

In a batch-type polymerization reactor, copolymerization of ethylene with 1-octene was carried out as described below.

In a 200 mL stainless steel reactor, which had been sufficiently dried and purged with nitrogen, charged was cyclohexane (91 mL) and 1-octene (8 mL). Then, 54.17 mM solution (5.5 mL) of modified methylaluminoxane-7 (modified MAO-7, 7 wt % Al Isopar solution, from Akzo Nobel) in toluene was added thereto. Then, the temperature of the reactor was raised to 140° C., and (dichloro)(pentamethylcyclopentadienyl)(2-(9'H-fluoren-2'-yl)phenoxy)titanium(IV) (5 mM solution in toluene) (0.98 mL) which had been synthesized from Preparation Example 3 and 4.07 mM solution of triphenylmethylinium tetrakispentafluorophenylborate (99%, Boulder Scientific) in toluene (0.74 mL) were sequentially added thereto. By means of ethylene, the pressure in the reactor was then made up to 30 kg/cm$^2$, with continual supply thereof to carry out polymerization. In one minute of the reaction, maximum temperature 166.5° C. was achieved. After 1 minute, 10 mL of ethanol containing 10 vol % of aqueous hydrochloric acid was added to quench the polymerization. Then, the mixture was stirred with 150 mL of ethanol for 1 hour, and the reaction product was filtered and isolated. The reaction product thus collected was dried in an vacuum oven at 60° C. for 8 hours to obtain 4.5 g of polymer. The polymer had the melting point of 79.9° C., melt index of 73, density of 0.8823 g/cc, and 1-octene content of 23.2% by weight.

EXAMPLES 4~8

In a continuous polymerization device, copolymerization of ethylene with 1-octene was carried out as described below.

As a single activation point catalyst, employed was (dichloro)(pentamethylcyclopentadienyl)(2-(9',9"-dimethylfluoren-2'-yl)phenoxy)titanium (IV) (synthesized from Preparation Example 1). The amounts of the catalyst used are shown in Table 1. Ti shows the single activation point catalyst, Al triisobutylaluminum as the cocatalyst, and B triphenylmethylinium tetrakispentafluorophenylborate, respectively. The catalyst was injected after being dissolved in toluene in a concentration of 0.2 g/L. The synthesis was carried out by using 1-octene as the comonomer. Conversion in the reactor was determined by gas chromatography analysis of the process stream after the reaction. The molecular weight (for a single activation point catalyst) was controlled as a function of the reactor temperature and 1-octene content. The conditions are shown in Table 1.

TABLE 1

|  | Ex. 4 | Ex. 5 | Ex. 6 | Ex. 7 | Ex. 8 |
| --- | --- | --- | --- | --- | --- |
| Flow rate of overall solution (kg/h) | 5 | 5 | 5 | 5 | 5 |
| Amount of ethylene | 10 | 10 | 10 | 10 | 10 |
| Proportion of 1-octene (1-octene/ethylene) | 0.3 | 0.3 | 0.3 | 0.3 | 0.3 |
| Amount of Ti (μmol/kg) | 6 | 5 | 4 | 3 | 2.5 |
| Al/Ti ratio | 30 | 35 | 44 | 58 | 58 |
| B/Ti ratio | 3 | 3 | 3 | 3 | 3 |
| Reaction temperature (° C.) | 151.6 | 151.2 | 152.0 | 149.8 | 152.2 |
| Conversion (%) | 97.0 | 95.6 | 92.4 | 88.8 | 80.6 |

TABLE 1-continued

|  | Ex. 4 | Ex. 5 | Ex. 6 | Ex. 7 | Ex. 8 |
| --- | --- | --- | --- | --- | --- |
| MI | 20.12 | 17.12 | 10.12 | 6.17 | 4.39 |
| Density | 0.8872 | 0.8976 | 0.8990 | 0.9003 | 0.9006 |

Ti: Ti in the single activation point catalyst
Al: Triisobutylaluminum as cocatalyst
B: Triphenylmethylinium tetrakispentafluorophenylborate as cocatalyst

EXAMPLE 9

In a batch-type polymerization reactor, copolymerization of ethylene with 1-octene was carried out as described below.

In a 200 mL stainless steel reactor, which had been sufficiently dried and purged with nitrogen, charged was cyclohexane (91 mL) and 1-octene (8 mL). Then, 54.17 mM solution (5.5 mL) of modified methylaluminoxane-7 (modified MAO-7, 7 wt % Al Isopar solution, from Akzo Nobel) in toluene was added thereto. Then, the temperature of the reactor was raised to 140° C., and (dichloro) (pentamethylcyclopentadienyl)(2-tert-butyl-6-(9',9"-dimethylfluoren-2'-yl)-4-methylphenoxy)titanium(IV) (5 mM solution in toluene) (0.98 mL) which had been synthesized from Preparation Example 4 and 4.07 mM solution of triphenylmethylinium tetrakispentafluorophenylborate (99%, Boulder Scientific) in toluene (0.74 mL) were sequentially added thereto. By means of ethylene, the pressure in the reactor was then made up to 30 kg/cm$^2$, with continual supply thereof to carry out polymerization. In one minute of the reaction, maximum temperature 168.5° C. was achieved. After 1 minute, 10 mL of ethanol containing 10 vol % of aqueous hydrochloric acid was added to quench the polymerization. Then, the mixture was stirred with 150 mL of ethanol for 1 hour, and the reaction product was filtered and isolated. The reaction product thus collected was dried in an vacuum oven at 60° C. for 8 hours to obtain 4.8 g of polymer. The polymer had the melting point of 70.2° C., melt index of 65, density of 0.8801 g/cc, and 1-octene content of 23.0% by weight.

As can be seen from the Examples 1 to 9, polymers having large weight average molecular weight can be produced under the condition of high temperature (at 140° C. or higher) with low molecular weight distribution, according to the invention. Particularly, one can successfully obtain low-density copolymers from ethylene and 1-octene.

Though the present invention is described in detail with referring to Examples as above, a person having ordinary skill in the art in the field of industry to which the invention belongs can make various modification without departing from the spirit or scope of the invention, which was defined by appended claims. Thus, any alteration or modification of the Examples of the invention to come would not depart from the technique of the present invention.

[Industrial Applicability]

The transition metal compound according to the invention or the catalyst composition comprising the compound can be easily produced in a simple synthetic procedure with economic advantage. Due to its excellent thermal stability, the catalyst maintains high catalytic activity even at high temperature having high copolymerization reactivity with other olefins to result in polymers with high molecular weight with high yield. Thus, the catalyst has higher commercial practicality than conventional metallocene or non-metallocene type single activation point catalysts already known. Therefore, the transition metal catalyst composition according to the present invention can be usefully employed in preparation of ethylene homopolymers or ethylene copolymer with α-olefin having different physical properties.

The invention claimed is:

1. A process for preparing ethylene homopolymers or copolymers of ethylene with α-olefin by using the transition metal compound,
wherein the transition metal compound is represented by Chemical Formula (1):

[Chemical Formula 1]

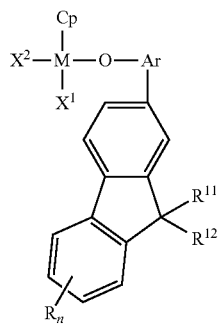

in the formula, M represents transition metal from Group 4 in the Periodic Table of Elements;
Cp represents cyclopentadienyl ring which is η⁵-linkable to M, or a fused ring containing a cyclopentadienyl ring, in which the cyclopentadienyl ring or the fused ring containing a cyclopentadienyl ring may be further substituted by (C1-C20)alkyl, (C6-C30)aryl, (C2-C20)alkenyl or (C6-C30)ar(C1-C20)alkyl;
Ar represents (C6-C14)arylene;
$R^{11}$ and $R^{12}$ independently represent hydrogen atom, (C1-C10)alkyl or (C6-C13)aryl(C1-C10)alkyl;
n is an integer from 0 to 3; R represents (C1-C10)alkyl, (C3-C10)cycloalkyl, (C6-C13)aryl, (C1-C10)alkyl(C6-C13)aryl, (C6-C13)ar(C1-C10)alkyl or (C1-C10) alkoxy; when n is 2 or 3, individual substituents of R may be same or different;
$X^1$ and $X^2$ independently represent halogen atom, (C1-C20)alkyl, (C3-C20)cycloalkyl, (C6-C30)aryl, (C6-C30)ar(C1-C20)alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20)alkylthio, (C6-C30)arylthio, (C1-C20)alkylphosphine, (C6-C30)arylphosphine, (C1-C20)alkylmercapto or (C6-C30)arylmercapto;
the alkyl, cycloalkyl, aryl, arylalkyl, alkoxy, aryloxy, alkylsiloxy, arylsiloxy, alkylamino, arylamino, alkylthio, arylthio, alkylphosphine, arylphosphine, alkylmercapto, arylmercapto of $R_n$, $X^1$ and $X^2$; and the arylene of Ar may be independently substituted by one or more substituent(s) selected from a group consisting of halogen, (C1-C20)alkyl, (C3-C20)cycloalkyl, (C6-C30)aryl, (C6-C30)ar(C1-C20)alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20)alkylthio, (C6-C30)arylthio, (C1-C20)alkylphosphine, (C6-C30)arylphosphine, (C1-C20)alkylmercapto and (C6-C30)arylmercapto; or each of them may be linked to an adjacent substituent via (C3-C12) alkylene or (C3-C12)alkenylene with or without a fused ring to form an alicyclic ring, or a monocyclic or polycyclic aromatic ring.

2. The process for preparing ethylene homopolymers or copolymers of ethylene with α-olefin according to claim 1, wherein Ar is selected from a group consisting of phenylene, naphthylene and fluorenylene.

3. The process for preparing ethylene homopolymers or copolymers of ethylene with α-olefin according to claim 1, wherein the transition metal compound is selected from those represented by one of Chemical Formulas (1-1) to (1-6):

[Chemical Formula 1-1]

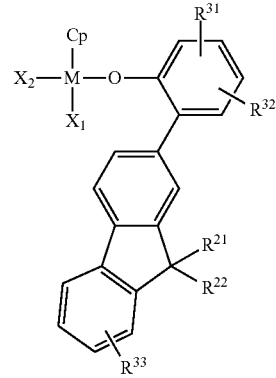

[Chemical Formula 1-2]

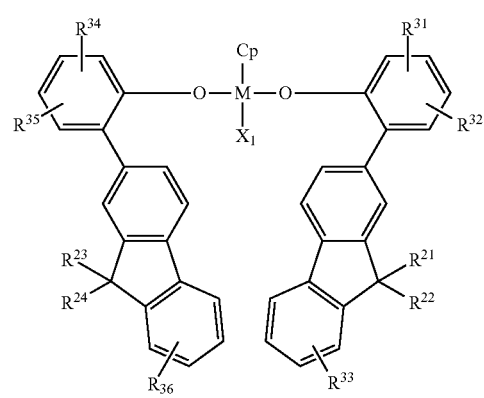

[Chemical Formula 1-3]

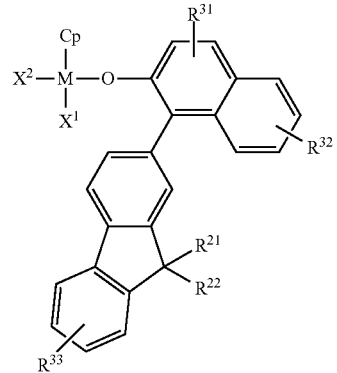

[Chemical Formula 1-4]

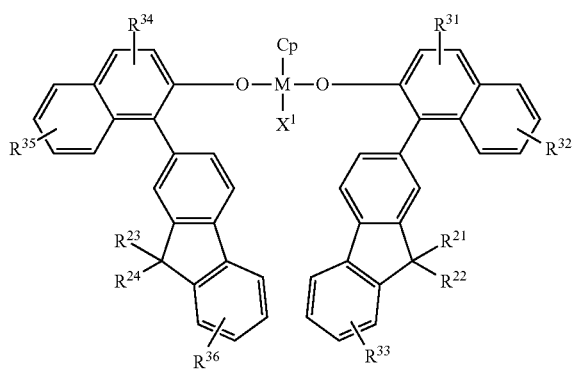

-continued

[Chemical Formula 1-5]

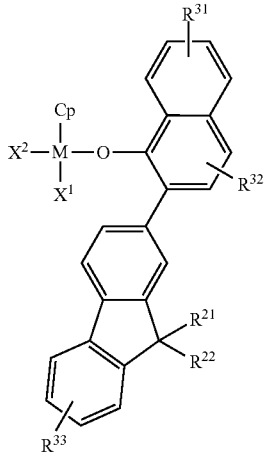

[Chemical Formula 1-6]

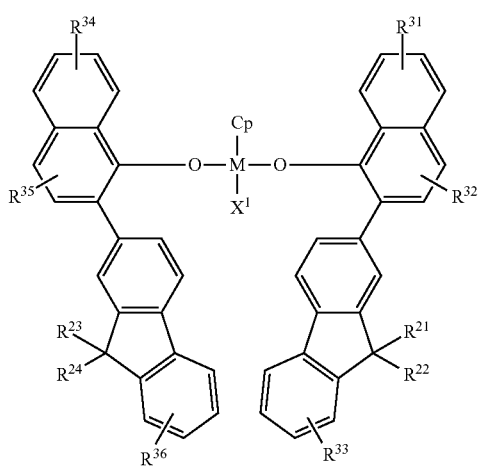

wherein, Cp represents cyclopentadienyl or pentamethylcyclopentadienyl;

M represents titanium, zirconium or hafnium;

$R^{21}$ through $R^{24}$ independently represent hydrogen or (C1-C10)alkyl;

$R^{31}$ through $R^{36}$ independently represent hydrogen atom, (C1-C10)alkyl, (C3-C10)cycloalkyl, (C6-C13)aryl, (C1-C10)alkyl(C6-C13)aryl, (C6-C13)ar(C1-C10)alkyl or (C1-C10)alkoxy;

$X^1$ and $X^2$ independently represent chloride, methyl, methoxy, isopropoxy, benzyl, fluorenyl, fluorenyloxy or dimethylamino.

4. The process for preparing ethylene homopolymers or copolymers of ethylene with α-olefin according to claim 1, wherein the transition metal compound is selected from the following compounds:

1-1-1

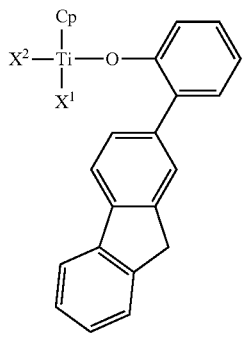

1-1-2

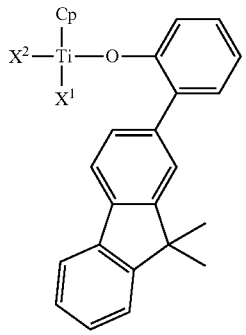

1-1-3

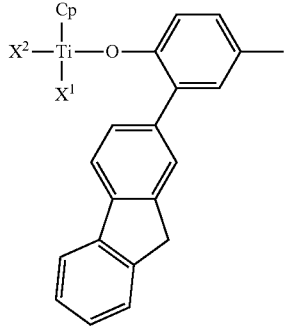

1-1-4

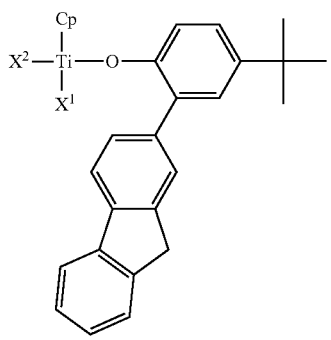

1-1-5 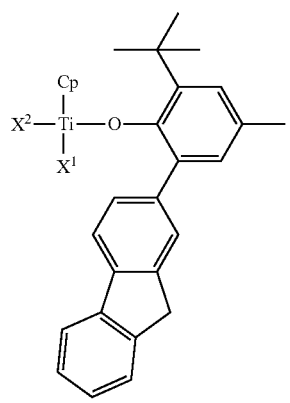
1-1-6 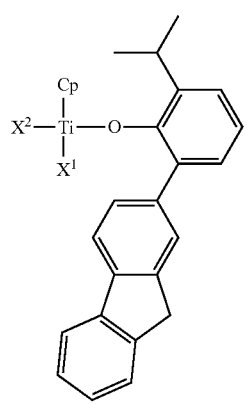
1-1-7 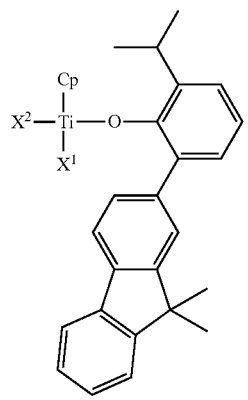
1-1-8 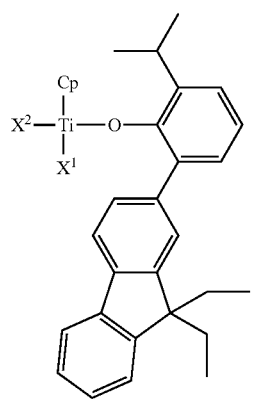
1-1-9 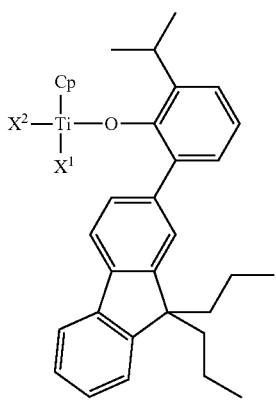
1-1-10 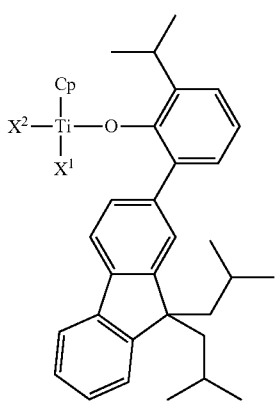
1-1-11 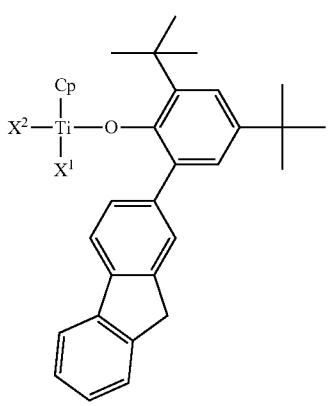
1-1-12 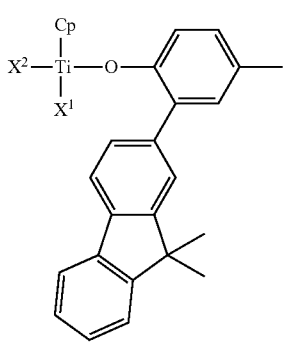

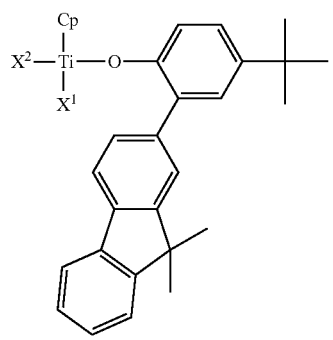
1-1-13
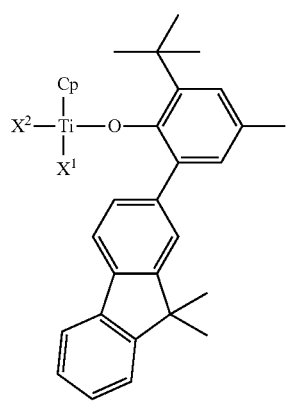
1-1-14
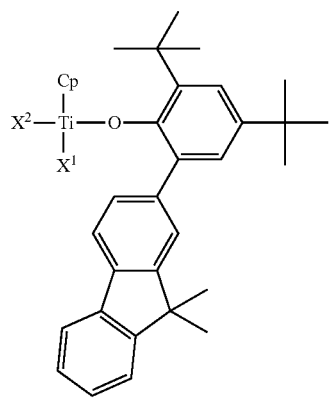
1-1-15
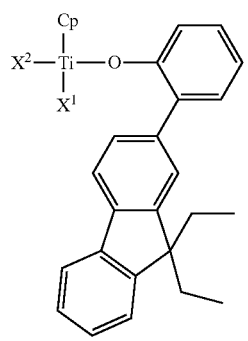
1-1-16
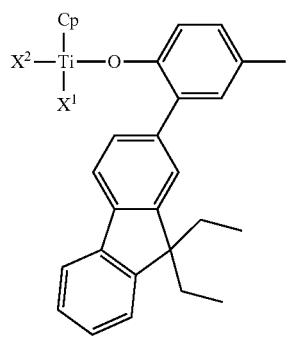
1-1-17
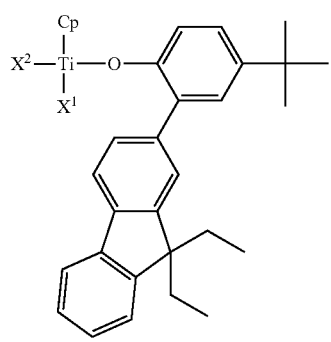
1-1-18
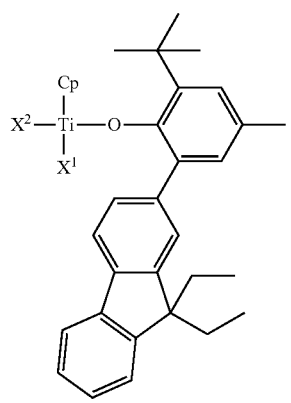
1-1-19
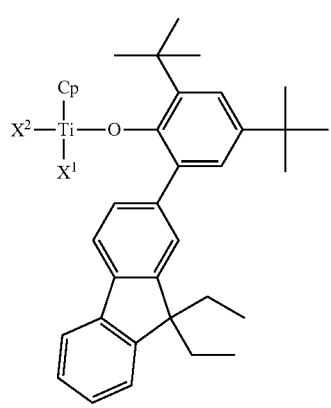
1-1-20

1-1-21 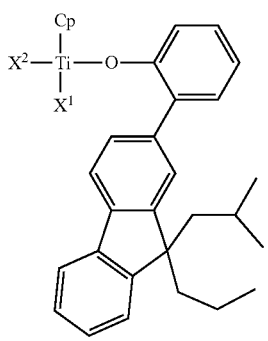
1-1-22 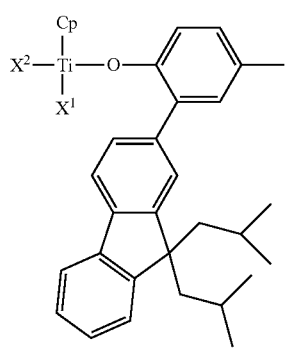
1-1-23 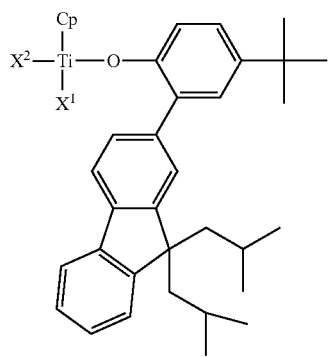
1-1-24 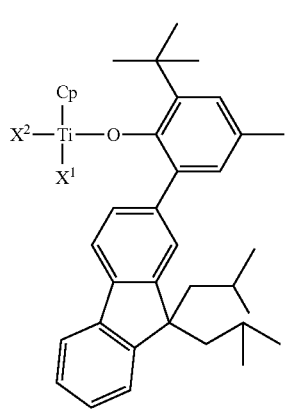
1-1-25 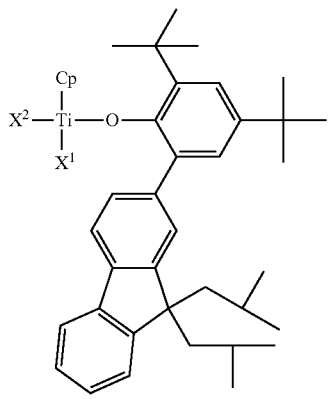
1-1-26 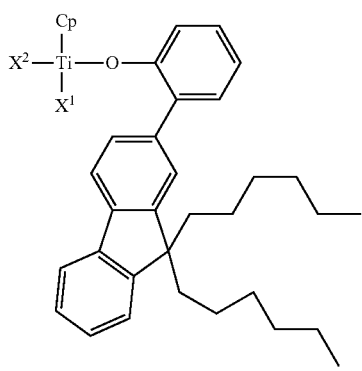
1-1-27 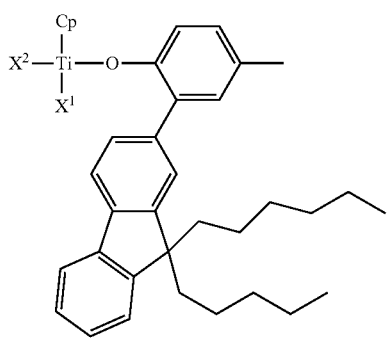
1-1-28 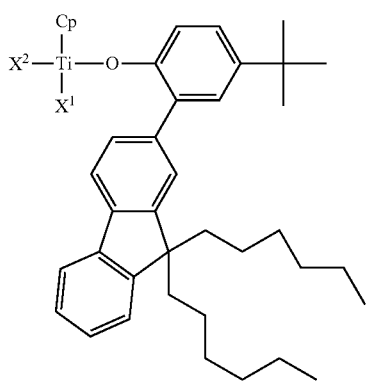

1-1-29 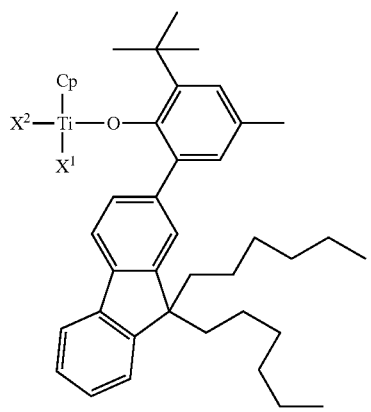
1-1-30 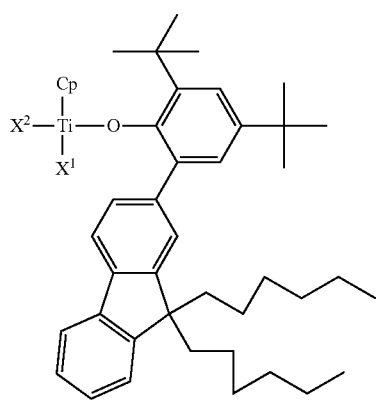
1-1-31 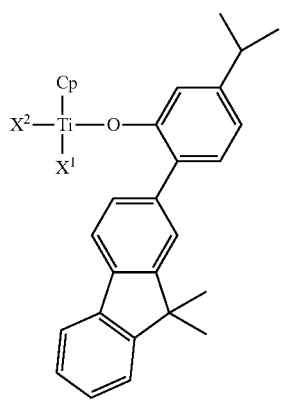
1-1-32 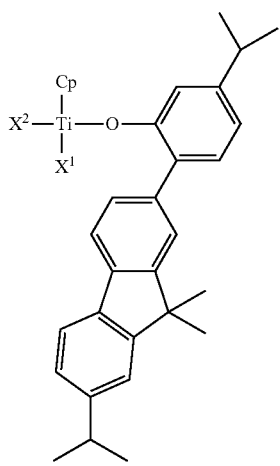
1-2-1 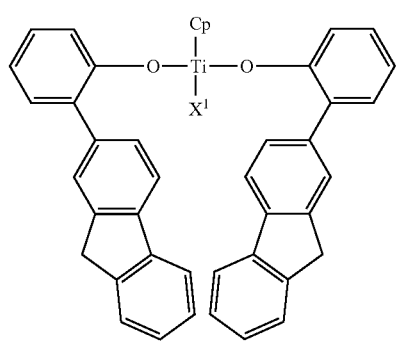
1-2-2 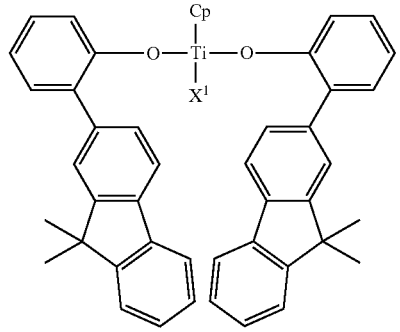
1-2-3

1-2-4
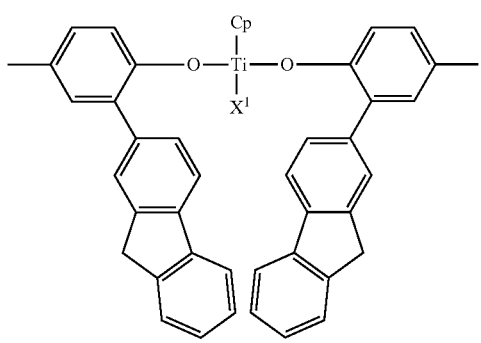
1-2-5
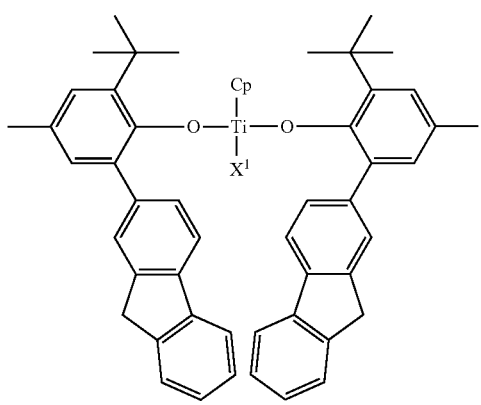
1-2-6
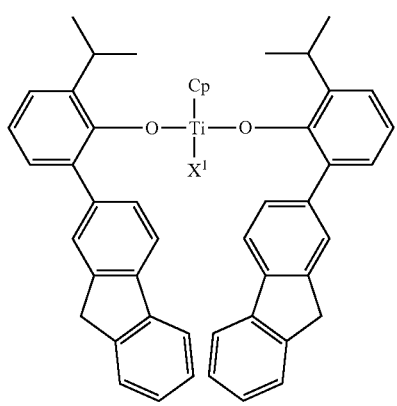
1-2-7
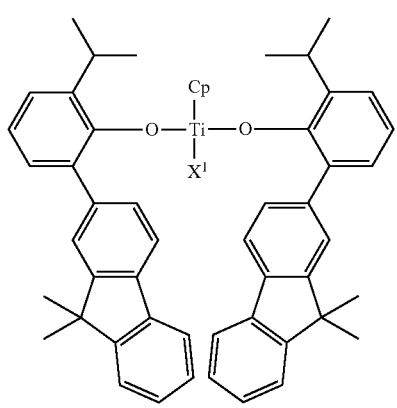
1-2-8
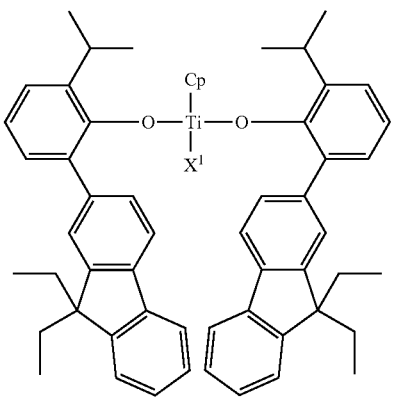
1-2-9
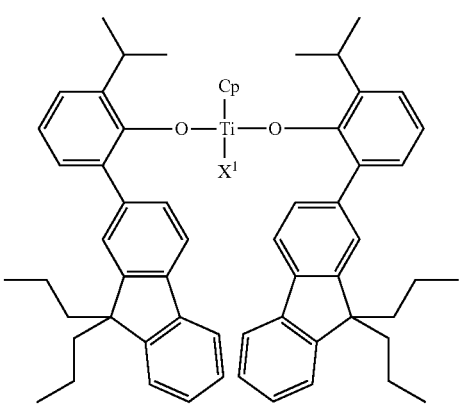
1-2-10
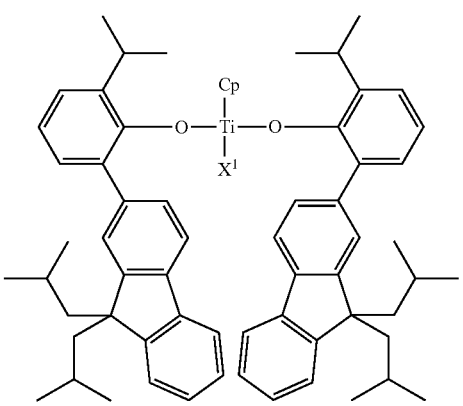
1-2-11
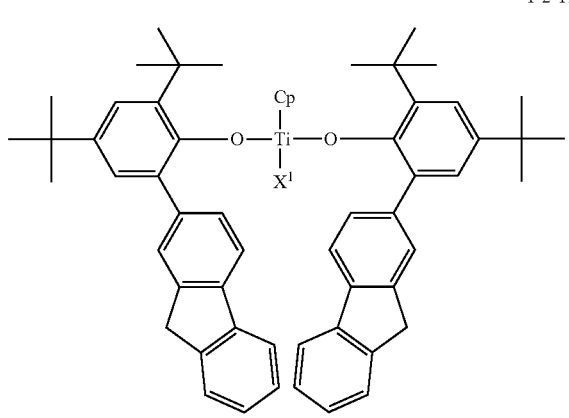

1-2-12
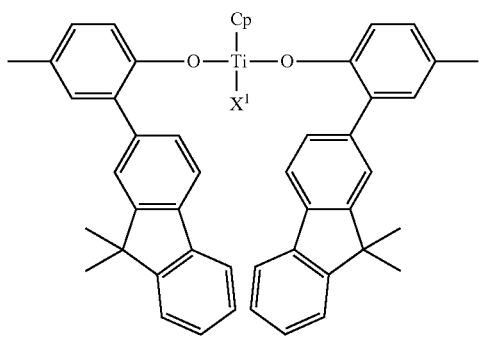
1-2-13
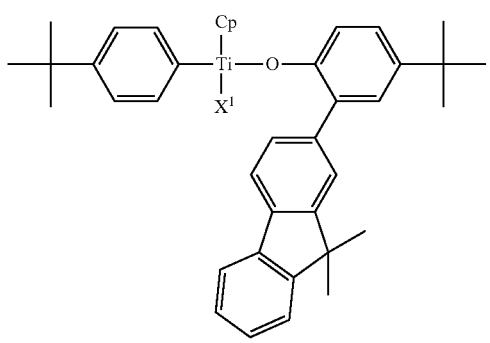
1-2-14
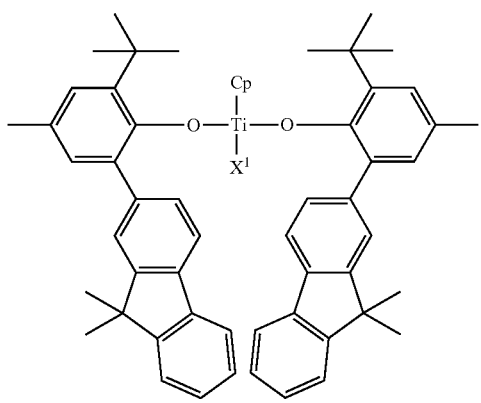
1-2-15
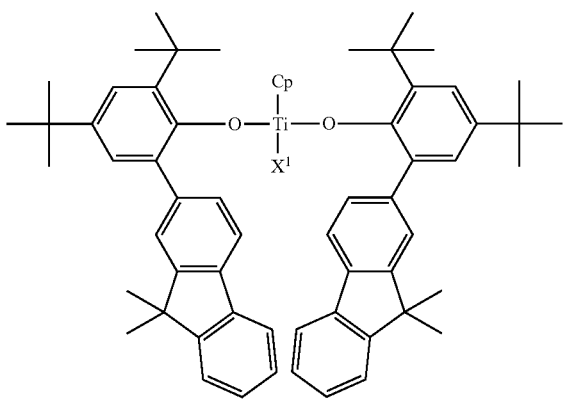
1-2-16
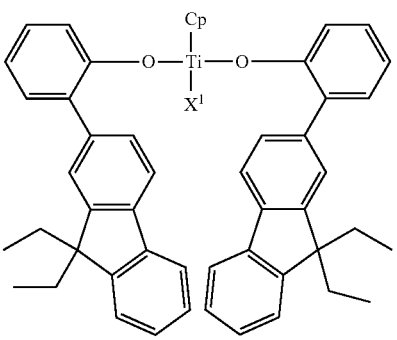
1-2-17
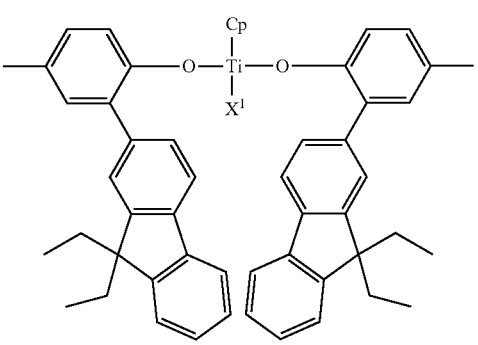
1-2-18
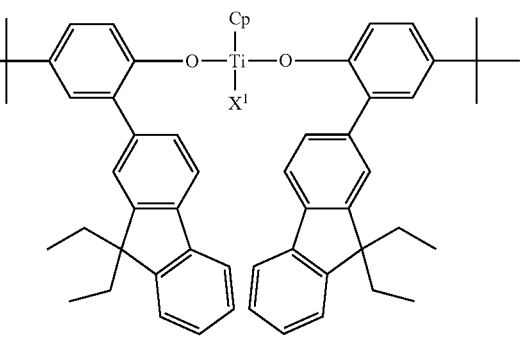
1-2-19
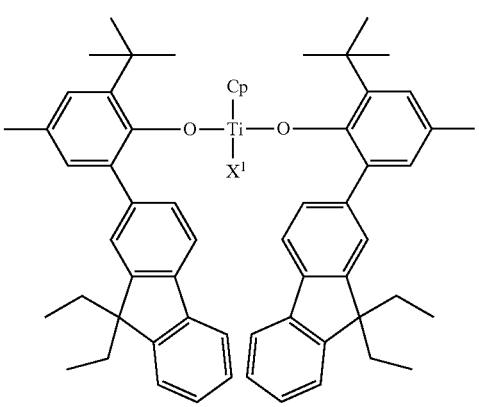

1-2-20
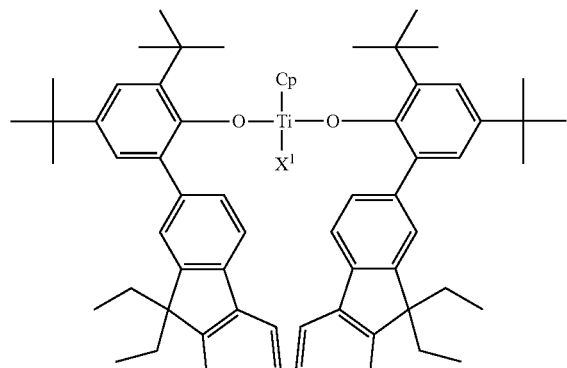
1-2-21
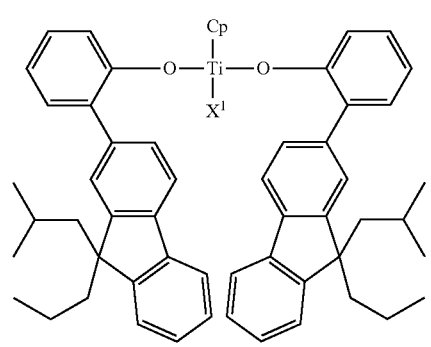
1-2-22
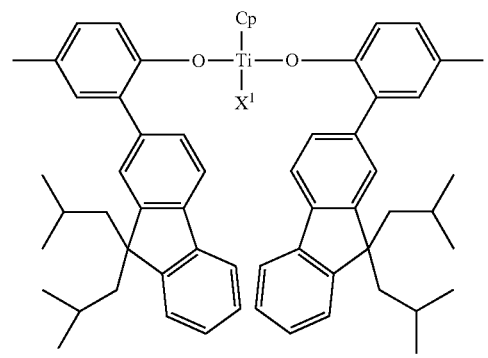
1-2-23
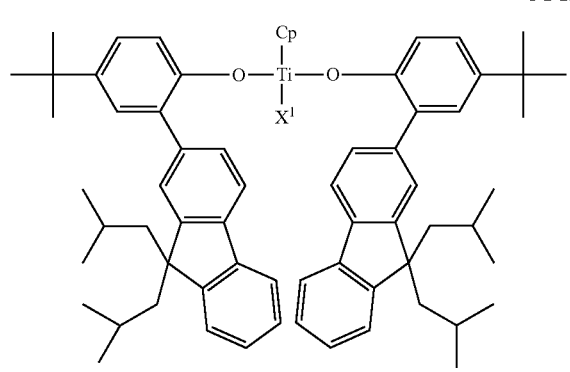
1-2-24
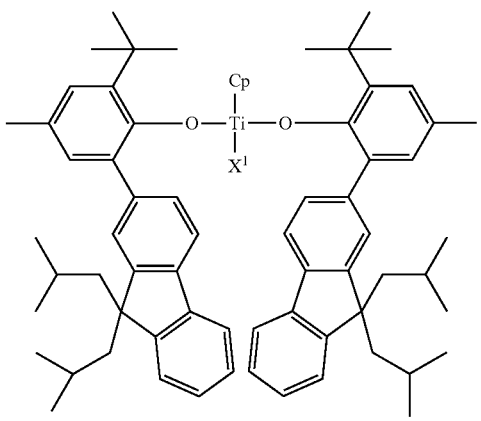
1-2-25
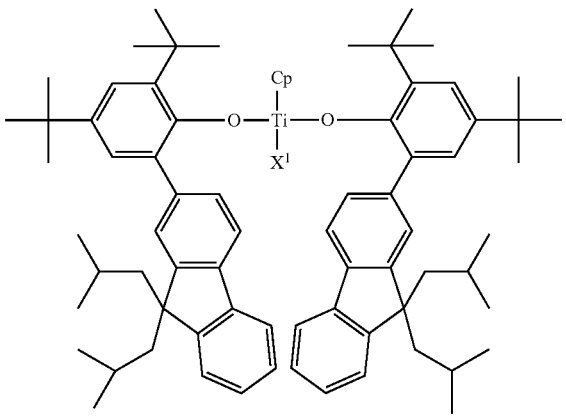
1-2-26
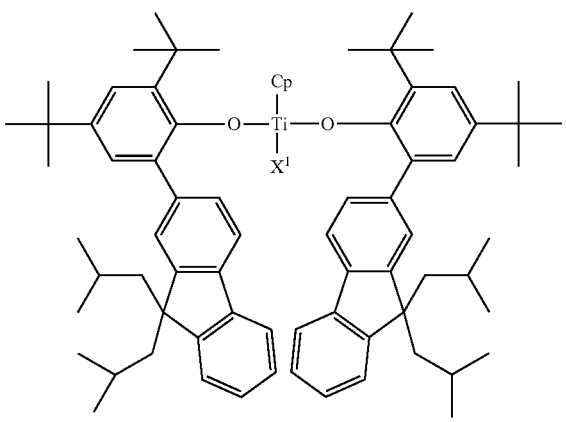

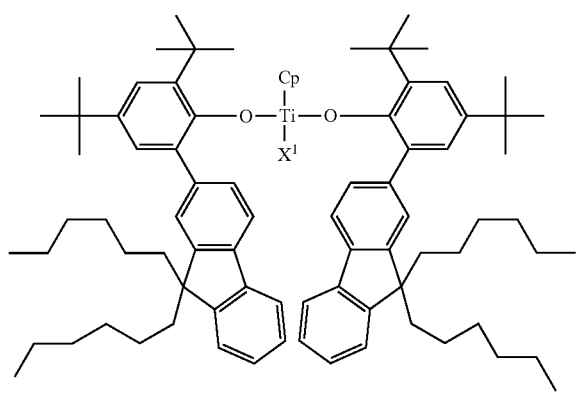
1-2-27
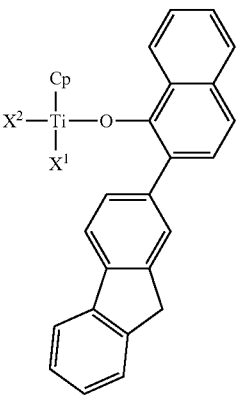
1-4-1
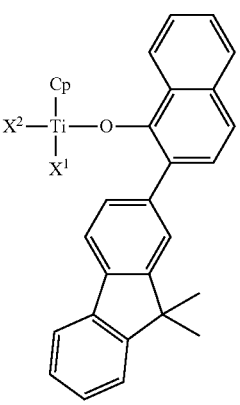
1-4-2
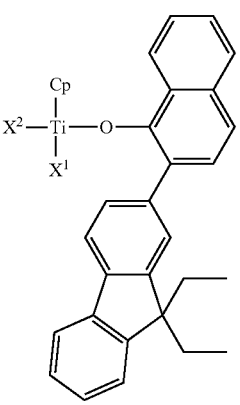
1-4-3
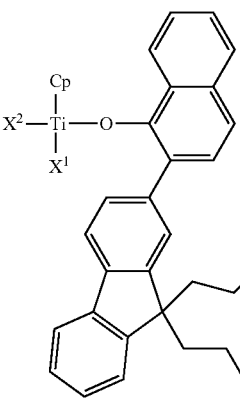
1-4-4

1-4-5
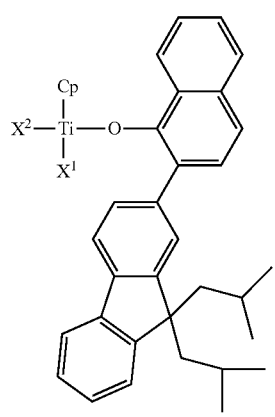
1-4-6
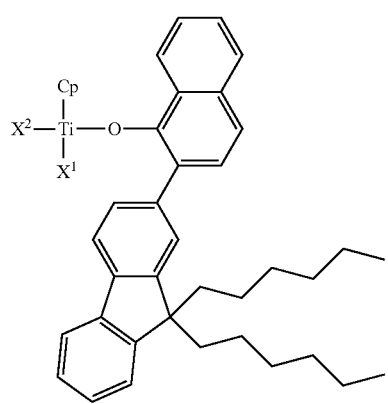
1-5-1
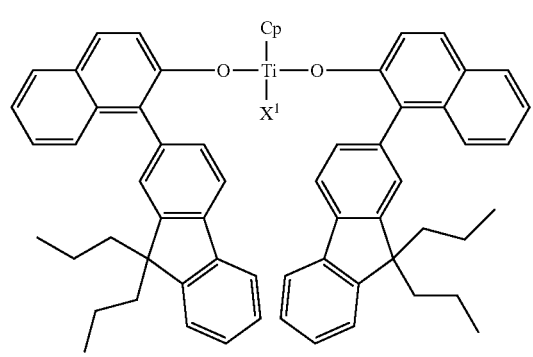
1-5-2
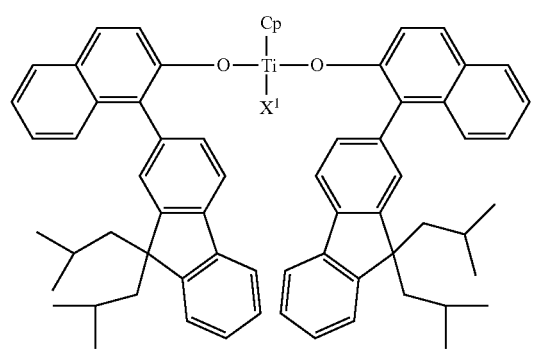
1-5-3
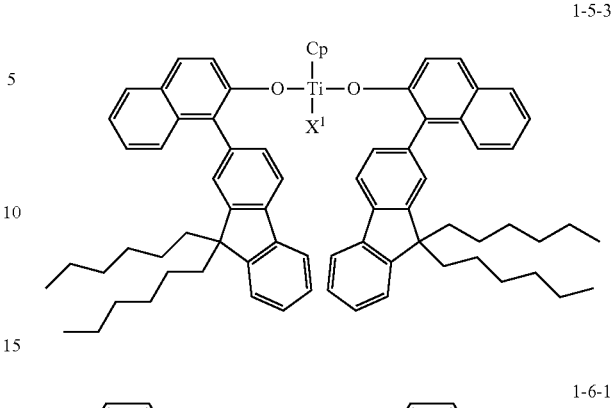
1-6-1
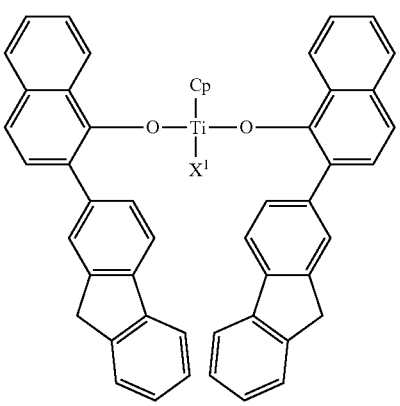
1-6-2
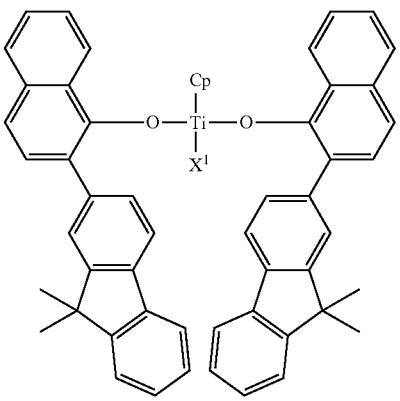
1-6-3
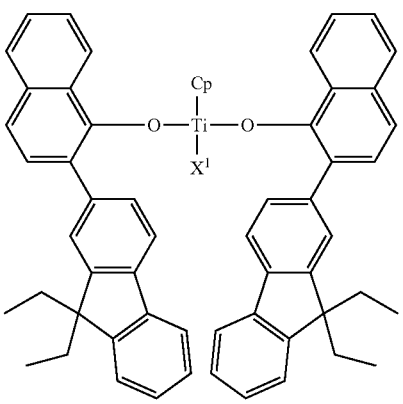

-continued

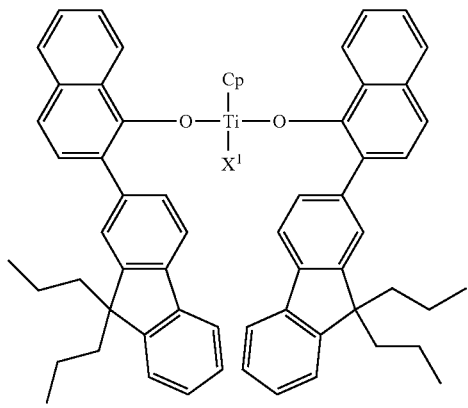

1-6-4

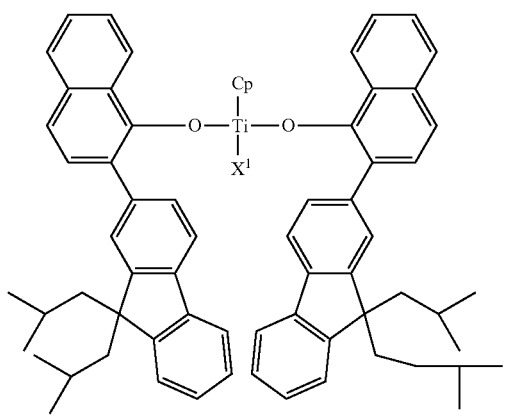

1-6-5

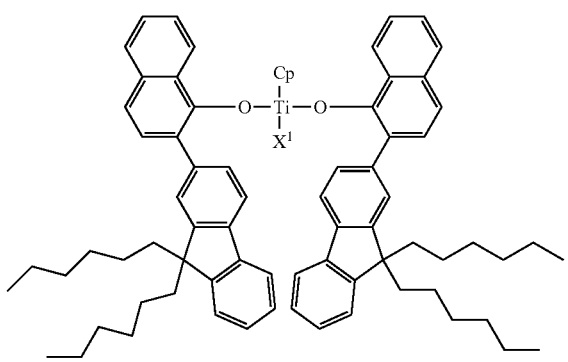

1-6-5 wherein, Cp represents cyclopentadienyl or pentamethylcyclopentadienyl; and $X^1$ and $X^2$ are independently selected from a group consisting of chloride, methyl, methoxy, isopropoxy, benzyl, fluorenyl, fluorenyloxy and dimethylamino.

5. A process for preparing ethylene homopolymers or copolymers of ethylene with α-olefin by using the transition metal catalyst composition which comprises the transition metal compound, and alkylaluminoxane or organoaluminum cocatalyst, or boron compound cocatalyst, or a mixture thereof, wherein the transition metal compound is represented by Chemical Formula (1):

[Chemical Formula 1]

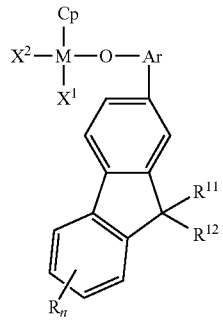

in the formula, M represents transition metal from Group 4 in the Periodic Table of Elements;

Cp represents cyclopentadienyl ring which is $\eta^5$-linkable to M, or a fused ring containing a cyclopentadienyl ring, in which the cyclopentadienyl ring or the fused ring containing a cyclopentadienyl ring may be further substituted by (C1-C20)alkyl, (C6-C30)aryl, (C2-C20)alkenyl or (C6-C30)ar(C1-C20)alkyl ;

Ar represents (C6-C14)arylene;

$R^{11}$ and $R^{12}$ independently represent hydrogen atom, (C1-C10)alkyl or (C6-C13)aryl(C1-C10)alkyl;

n is an integer from 0 to 3; R represents (C1-C10)alkyl, (C3-C10)cycloalkyl, (C6-C13)aryl, (C1-C10)alkyl(C6-C13)aryl, (C6-C13)ar(C1-C10)alkyl or (C1-C10) alkoxy; when n is 2 or 3, individual substituents of R may be same or different;

$X^1$ and $X^2$ independently represent halogen atom, (C1-C20)alkyl, (C3-C20)cycloalkyl, (C6-C30)aryl, (C6-C30)ar(C1-C20)alkyl, (C1-C20)alkoxy, (C6-C30)aryloxy, (C3-C20)alkylsiloxy, (C6-C30)arylsiloxy, (C1-C20)alkylamino, (C6-C30)arylamino, (C1-C20) alkylthio, (C6-C30)arylthio, (C1-C20)alkylphosphine, (C6-C30)arylphosphine, (C1-C20)alkylmercapto or (C6-C30)arylmercapto;

the alkyl, cycloalkyl, aryl, arylalkyl, alkoxy, aryloxy, alkylsiloxy, arylsiloxy, alkylamino, arylamino, alkylthio, arylthio, alkylphosphine, arylphosphine, alkylmercapto, arylmercapto of $R_n$, $X^1$ and $X^2$; and the arylene of Ar may be independently substituted by one or more substituent(s) selected from a group consisting of halogen, (C1-C20)alkyl, (C3-C20)cycloalkyl, (C6-C30) aryl, (C6-C30)ar(C1-C20)alkyl, (C1-C20)alkoxy, (C6-C30)aryloxy, (C3-C20)alkylsiloxy, (C6-C30) arylsiloxy, (C1-C20)alkylamino, (C6-C30)arylamino, (C1-C20)alkylthio, (C6-C30)arylthio, (C1-C20)alkylphosphine, (C6-C30)arylphosphine, (C1-C20)alkylmercapto and (C6-C30)arylmercapto; or each of them may be linked to an adjacent substituent via (C3-C12) alkylene or (C3-C12)alkenylene with or without a fused ring to form an alicyclic ring, or a monocyclic or polycyclic aromatic ring.

* * * * *